US008457352B2

(12) United States Patent
Hennessey et al.

(10) Patent No.: US 8,457,352 B2
(45) Date of Patent: Jun. 4, 2013

(54) METHODS AND APPARATUS FOR ESTIMATING POINT-OF-GAZE IN THREE DIMENSIONS

(75) Inventors: Craig A. Hennessey, Vancouver (CA); Peter D. Lawrence, Vancouver (CA)

(73) Assignee: The University of British Columbia, Vancouver (CA)

( * ) Notice: Subject to any disclaimer, the term of this patent is extended or adjusted under 35 U.S.C. 154(b) by 493 days.

(21) Appl. No.: 12/600,238

(22) PCT Filed: May 23, 2008

(86) PCT No.: PCT/CA2008/000987
§ 371 (c)(1),
(2), (4) Date: May 25, 2010

(87) PCT Pub. No.: WO2008/141460
PCT Pub. Date: Nov. 27, 2008

(65) Prior Publication Data
US 2011/0228975 A1    Sep. 22, 2011

Related U.S. Application Data

(60) Provisional application No. 61/071,372, filed on Apr. 24, 2008, provisional application No. 60/939,840, filed on May 23, 2007.

(51) Int. Cl.
*G06K 9/00* (2006.01)
(52) U.S. Cl.
USPC ........................................................ 382/103
(58) Field of Classification Search
USPC .................... 352/100–107; 348/169–174
See application file for complete search history.

(56) References Cited

U.S. PATENT DOCUMENTS

| 4,836,670 | A | 6/1989 | Hutchinson |
| 5,231,674 | A | 7/1993 | Cleveland et al. |
| 5,428,413 | A | 6/1995 | Shindo |
| 5,471,542 | A | 11/1995 | Ragland |
| 5,481,622 | A | 1/1996 | Gerhardt |
| 6,152,563 | A | 11/2000 | Hutchinson et al. |

(Continued)

FOREIGN PATENT DOCUMENTS

| WO | 2004045399 | 6/2004 |
| WO | 2005063114 | 7/2005 |
| WO | PCT/JP04/19311 | * 7/2005 |

OTHER PUBLICATIONS

L. Young and D. Sheena, "Methods & designs: survey of eye movement recording methods," Behav. Res. Methods Instrum., vol. 5, pp. 397-429, 1975.

(Continued)

*Primary Examiner* — Atiba O Fitzpatrick
(74) *Attorney, Agent, or Firm* — Oyen Wiggs Green & Mutala LLP

(57) ABSTRACT

Methods for determining a point-of-gaze (POG) of a user in three dimensions are disclosed. In particular embodiments, the methods involve: presenting a three-dimensional scene to both eyes of the user; capturing image data including both eyes of the user; estimating first and second line-of-sight (LOS) vectors in a three-dimensional coordinate system for the user's first and second eyes based on the image data; and determining the POG in the three-dimensional coordinate system using the first and second LOS vectors.

42 Claims, 12 Drawing Sheets

U.S. PATENT DOCUMENTS

| | | |
|---|---|---|
| 6,574,352 B1 | 6/2003 | Skolmoski |
| 6,578,962 B1 | 6/2003 | Amir et al. |
| 6,611,283 B1 | 8/2003 | Isonuma |
| 6,659,611 B2 | 12/2003 | Amir et al. |
| 2003/0098954 A1 | 5/2003 | Amir et al. |
| 2006/0110008 A1 | 5/2006 | Vertegaal et al. |
| 2006/0210111 A1 | 9/2006 | Cleveland et al. |
| 2006/0239670 A1 | 10/2006 | Cleveland |
| 2007/0279590 A1 | 12/2007 | Ebisawa |

OTHER PUBLICATIONS

T. Hutchinson, J. White, W. Martin, K. Reichert, and L. Frey, "Human-computer interaction using eye-gaze input," Systems, Man and Cybernetics, IEEE Transactions on, vol. 19, No. 6, pp. 1527-1534, Nov.-Dec. 1989.

S.-W. Shih and J. Liu, "A novel approach to 3-d gaze tracking using stereo cameras," Systems, Man and Cybernetics, Part B, IEEE Transactions on, vol. 34, No. 1, pp. 234-245, Feb. 2004.

D. Beymer and M. Flickner, "Eye gaze tracking using an active stereo head," in IEEE Computer Society Conference on Computer Vision and Pattern Recognition, vol. 2, Jun. 18-20, 2003, pp. II.

C. Hennessey, B. Noureddin, and P. Lawrence, "A single camera eye-gaze tracking system with free head motion," in Proceedings of the 2006 symposium on Eye tracking research & applications. New York, NY, USA: ACM Press, 2006, pp. 87-94.

C.H. Morimoto, A. Amir, M. Flickner, "Detecting Eye Position and Gaze from a Single Camera and 2 Light Sources," 16th International Conference on Pattern Recognition (ICPR'02)—vol. 4, 2002, p. 40314.

Z. Zhu and Q. Ji, "Eye Gaze Tracking Under Natural Head Movements," Proceedings of the 2005 IEEE Computer Society Conference on Computer Vision and Pattern Recognition, 2005.

E. Guestrin and M. Eizenman, "General theory of remote gaze estimation using the pupil center and corneal reflections," Biomedical Engineering, IEEE Transactions on, vol. 53, No. 6, pp. 1124-1133, Jun. 2006.

M. Halle, "Autostereoscopic displays and computer graphics," SIGGRAPH Comput. Graph., vol. 31, No. 2, pp. 58-62, 1997.

A. T. Duchowski, V. Shivashankaraiah, T. Rawls, A. K. Gramopadhye, B. J. Melloy, and B. Kanki, "Binocular eye tracking in virtual reality for inspection training," in Proceedings of the 2000 symposium on Eye tracking research & applications. New York, NY, USA: ACM Press, 2000, pp. 89-96.

K. Essig, M. Pomplun, and H. Ritter, "Application of a novel neural approach to 3d gaze tracking: Vergence eye-movements in autostereograms," in Proceedings of the 26thl Meeting of the Cognitive Science Society, K. Forbus, D. Gentner, and T. Regier, Eds., 2004, pp. 357-362.

K. Essig, M. Pomplun, and H. Ritter, "A neural network for 3d gaze recording with binocular eyetrackers," International Journal of Parallel, Emergent and Distributed Systems (accepted), 2006.

Y.-M. Kwon and K.-W. Jeon, "Gaze computer interaction on stereo display," in Proceedings of the 2006 ACM SIGCHI international conference on Advances in computer entertainment technology. New York, NY, USA: ACM Press, 2006, p. 99.

C. Hennessey, "Eye-Gaze Tracking With Free Head Motion", A Thesis Submitted in Partial Fulfilment of the Requirements for the Degree of Master of Applied Science in The Faculty of Graduate Studies, Aug. 2005.

F. Arnold, "Reviews and Abstract of Literature", The Journal of Philosophy, Physiological and Scientific Methods, vol. 2, No. 17, Aug. 17, 1905.

C. Goldthwait, "Relation of Eye-Movements to Visual Imagery", The American Journal of Psychology, vol. 45, No. 1. Jan. 1933, pp. 106-110.

A. Duchowski, "A Breadth-First Survey of Eye Tracking Applications", Behaviours Research Methods, Instruments, and Computers, 2002, pp.

C. Chen and C. Hennessey, "Online Eye-Gaze Usability Evaluation of Gmail; Are Mobile Interfaces Easier to Use with Eye-Trackers?", Proceedings of the 33rd Conference of the Canadian Medical and Biological Engineering Society, Jun. 2010. Conference Paper.

F. Macdonald, E. Guld and C. Hennessey, "A Study of Applying Gaze-Tracking Control to Motorized Assistive Devices", Proceedings of the 33rd Conference of the Canadian Medical and Biological Engineering Society, Jun. 2010. Conference Paper.

C. Hennessey and A. Duchowski, "An Open Source Eye-gaze Interface: Expanding the Adoption of Eye-gaze in Everyday Applications", Proceedings of the 2010 Symposium on Eye Tracking Research & Applications, pp. 81-84, Mar. 2010. Conference Paper.

C. Hennessey and P. Lawrence, "Improving the Accuracy and Reliability of Remote System-Calibration-Free Eye-gaze Tracking", IEEE Transactions on Biomedical Engineering. vol. 56, No. 6, pp -, Jun. 2009.

C. Hennessey and P. Lawrence, "Non-Contact Binocular Eye-Gaze Tracking for Point-of-Gaze Estimation in Three Dimensions", IEEE Transactions on Biomedical Engineering. vol. 56, No. 3, pp. 790-799, Mar. 2009.

C. Hennessey, "Point-of-Gaze Estimation in Three Dimensions", Doctor of Philosophy, Electrical and Computer Engineering, University of British Columbia, 2008.

C. Hennessey, B.Noureddin and P. Lawrence, "Fixation Precision in High-Speed Noncontact Eye-Gaze Tracking", IEEE Transactions on Systems, Man and Cybernetics—Part B. vol. 38, No. 2, pp. 289-298, Apr. 2008.

C. Hennessey and P. Lawrence, "3D Point-of-Gaze Estimation on a Volumetric Display", Proceedings of the 2008 Symposium on Eye Tracking Research & Applications, pp. 59-59, 2008.

\* cited by examiner

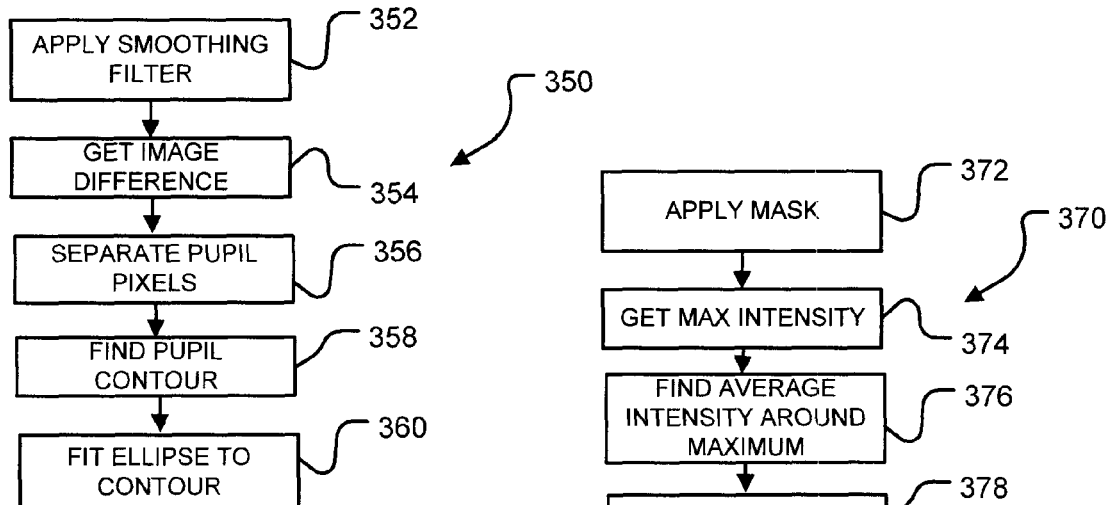
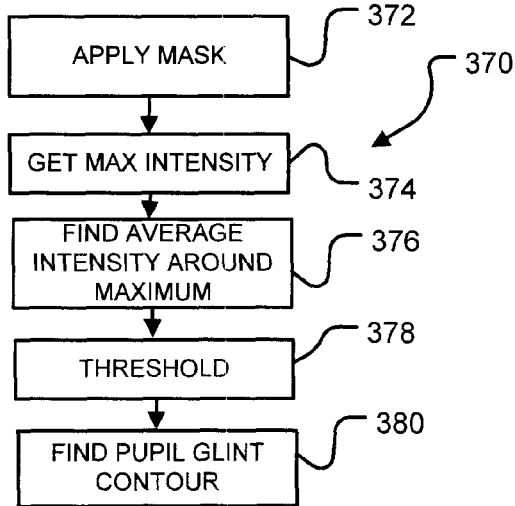
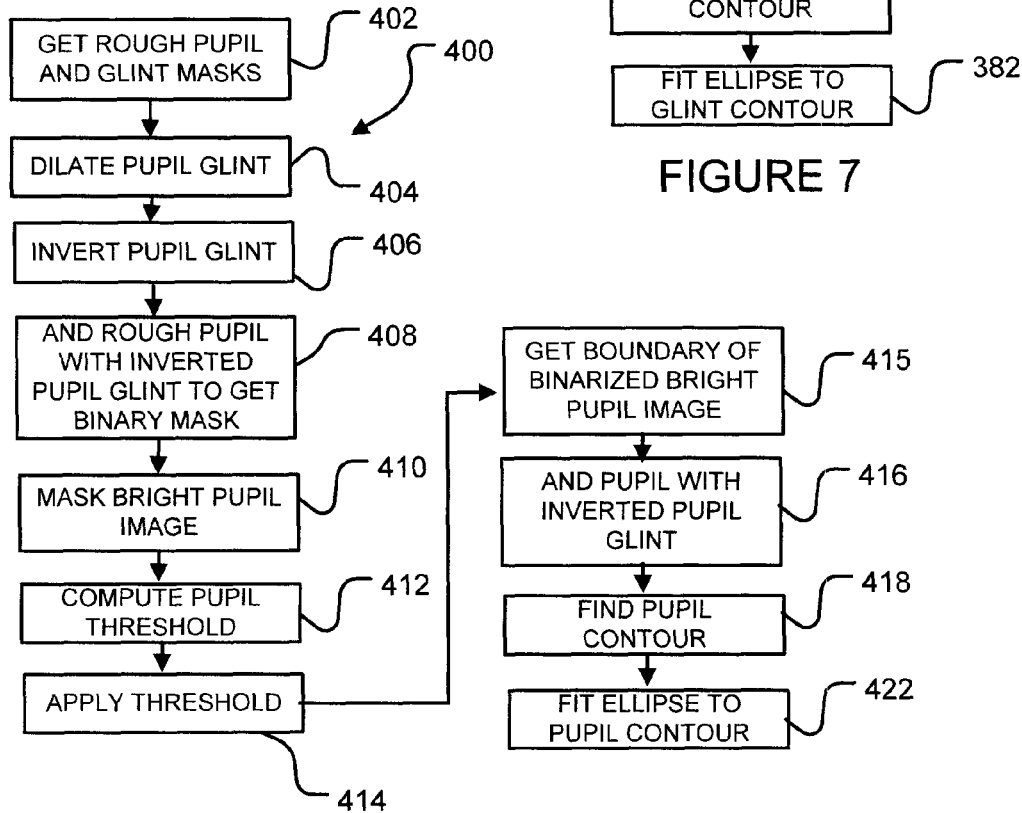
FIGURE 6
FIGURE 7
FIGURE 8

METHODS AND APPARATUS FOR ESTIMATING POINT-OF-GAZE IN THREE DIMENSIONS

RELATED APPLICATIONS

This application claims priority from U.S. application No. 60/939,840 filed 23 May 2007 and U.S. application No. 61/071,372 filed 24 Apr. 2008, both of which are hereby incorporated herein by reference.

TECHNICAL FIELD

The invention relates to sensing and tracking eye-gaze characteristics and to methods and apparatus for using this information to estimate a point-of-gaze in three dimensions.

BACKGROUND

Common techniques for interaction between humans and machines include hand-operated user interface devices, such as keyboards, buttons, joysticks and pointing devices (e.g. a mouse). Recent developments in eye-gaze tracking systems can determine the line-of-sight (LOS) vector of an individual's eye. This LOS information can be used as a control tool for human machine interaction. There are a number of advantages of using eye-gaze tracking information as a control tool. These advantages include: the intuitive link between the visual system of the eye and the resultant images in the brain; the speed of eye movement relative to moving a hand-operated interaction device (i.e. users typically look at the desired destination of a hand-operated device prior to moving the hand-operated device); and the possibility that eye-gaze tracking techniques may be used by severely disabled individuals.

A number of other applications for eye-gaze tracking systems include, without limitation: psychological and physiological research into the connection between eye movements and perceptual and/or cognitive processes; the analysis of driver awareness; research into the effectiveness of advertising and website layouts; and gaze contingent displays.

A number of prior art references describe various techniques for eye-gaze tracking. These references include:

A. T. Duchowski, *Eye Tracking Methodology: Theory and Practice*. Springer-Verlag, 2003.

L. Young and D. Sheena, "Methods & designs: survey of eye movement recording methods," *Behav. Res. Methods Instrum.*, vol. 5, pp. 397-429, 1975.

R. Jacob and K. Karn, *The Mind's Eye: Cognitive and Applied Aspects of Eye Movement Research*. Amsterdam: Elsevier Science, 2003, ch. Eye Tracking in Human-Computer Interaction and Usability Research: Ready to Deliver the Promises (Section Commentary), pp. 573-605.

T. Hutchinson, J. White, W. Martin, K. Reichert, and L. Frey, "Human-computer interaction using eye-gaze input," *Systems, Man and Cybernetics, IEEE Transactions on*, vol. 19, no. 6, pp. 1527-1534, November-December 1989.

S.-W. Shih and J. Liu, "A novel approach to 3-d gaze tracking using stereo cameras," *Systems, Man and Cybernetics, Part B, IEEE Transactions on*, vol. 34, no. 1, pp. 234-245, February 2004.

D. Beymer and M. Flickner, "Eye gaze tracking using an active stereo head," in *IEEE Computer Society Conference on Computer Vision and Pattern Recognition*, vol. 2, 18-20 June 2003, pp. II-451-8vol. 2.

C. Hennessey, B. Noureddin, and P. Lawrence, "A single camera eye-gaze tracking system with free head motion," in *Proceedings of the 2006 symposium on Eye tracking research & applications*. New York, N.Y., USA: ACM Press, 2006, pp. 87-94.

C. H. Morimoto, A. Amir, M. Flickner, "Detecting Eye Position and Gaze from a Single Camera and 2 Light Sources," 16*th International Conference on Pattern Recognition (ICPR '02)*-Volume 4, 2002, p. 40314.

Z. Zhu and Q. Ji, "Eye Gaze Tracking Under Natural Head Movements," *Proceedings of the 2005 IEEE Computer Society Conference on Computer Vision and Pattern Recognition*, 2005.

E. Guestrin and M. Eizenman, "General theory of remote gaze estimation using the pupil center and corneal reflections," *Biomedical Engineering, IEEE Transactions on*, vol. 53, no. 6, pp. 1124-1133, June 2006.

A. T. Duchowski, V. Shivashankaraiah, T. Rawls, A. K. Gramopadhye, B. J. Melloy, and B. Kanki, "Binocular eye tracking in virtual reality for inspection training," in *Proceedings of the 2000 symposium on Eye tracking research & applications*. New York, N.Y., USA: ACM Press, 2000, pp. 89-96.

K. Essig, M. Pomplun, and H. Ritter, "Application of a novel neural approach to 3d gaze tracking: Vergence eye-movements in autostereograms," in *Proceedings of the 26thl Meeting of the Cognitive Science Society*, K. Forbus, D. Gentner, and T. Regier, Eds., 2004, pp. 357-362.

K. Essig, M. Pomplun, and H. Ritter, "A neural network for 3d gaze recording with binocular eyetrackers," *International Journal of Parallel, Emergent and Distributed Systems* (accepted), 2006.

Y.-M. Kwon and K.-W. Jeon, "Gaze computer interaction on stereo display," in Proceedings of the 2006 ACM *SIGCHI international conference on Advances in computer entertainment technology*. New York, N.Y., USA: ACM Press, 2006, p. 99.

PCT publication No. WO04/045399 (Elvesjö et al.).
U.S. Pat. No. 4,386,670 (Hutchinson).
U.S. Pat. No. 5,231,674 (Cleveland et al.).
U.S. Pat. No. 5,471,542 (Ragland).
U.S. Pat. No. 5,428,413 (Shindo).
U.S. Pat. No. 6,152,563 (Hutchinson et al.).
U.S. Pat. No. 6,659,611 (Amir et al.).
U.S. Pat. No. 5,481,622 (Gerhardt).
U.S. Pat. No. 6,578,962 (Amir et al.).

Some of these prior art eye-gaze tracking systems may be used to detect LOS information for one of a user's eyes when the user's eye is fixated at a particular location (referred to as a point-of-gaze (POG)). An eye may be said to be "fixated" on a POG when the POG is imaged onto the eye's fovea and the motion of the eye is stabilized. To the extent that prior art eye-gaze tracking systems are used to estimate a POG using LOS information, the LOS is only used to estimate the POG in two dimensions. For example, where a user's eye is fixated on a two-dimensional monitor screen, the POG may be determined to be the location where the LOS vector intersects with the plane of the monitor screen.

Two-dimensional POG estimation may be satisfactory for interacting with standard two-dimensional human-machine interface environments (e.g. monitor screens). However, there are a number of continually improving three dimensional display technologies, such as volumetric displays and parallax beam splitter displays, for example, which may provide three-dimensional human-machine interface environments—see, for example, M. Halle, "Autostereoscopic displays and computer graphics," *SIGGRAPH Comput. Graph.*, vol. 31, no. 2, pp. 58-62, 1997. Such three-dimensional user interface environments could provide users with a much richer experience (i.e. more functionality) than existing two-dimensional user interface environments.

For this and other reasons, there is a general desire to provide methods and apparatus for POG estimation in three dimensions.

BRIEF DESCRIPTION OF THE DRAWINGS

In drawings which depict non-limiting embodiments of the invention:

FIG. 6 schematically depicts a particular embodiment of a method for obtaining rough pupil characteristics from the image data suitable for use with the method of FIG. 4;

FIG. 7 schematically depicts a particular embodiment of a method for obtaining pupil glint information from the image data suitable for use with the method of FIG. 4;

FIG. 8 schematically depicts a particular embodiment of a method for obtaining fine pupil characteristics from the image data suitable for use with the method of FIG. 4;

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Particular aspects of the invention provide methods and apparatus for estimating the POG of a user in three dimensions. One aspect of the invention provides a method for determining point-of-gaze (POG) of a user in three dimensions wherein the method comprises: presenting a three-dimensional scene to both of the eyes of the user; capturing image data which includes image(s) of both eyes of the user; estimating first and second line-of-sight (LOS) vectors in a three-dimensional coordinate system for the user's first and second eyes based on the image data; and determining the three-dimensional POG in the three-dimensional coordinate system using the first and second LOS vectors. In some embodiments, the three-dimensional scene presented to both of the user's eyes is the real world and the three-dimensional coordinate system is a system for identifying the location of point(s) or regions or the like in the real world.

Figure 1:
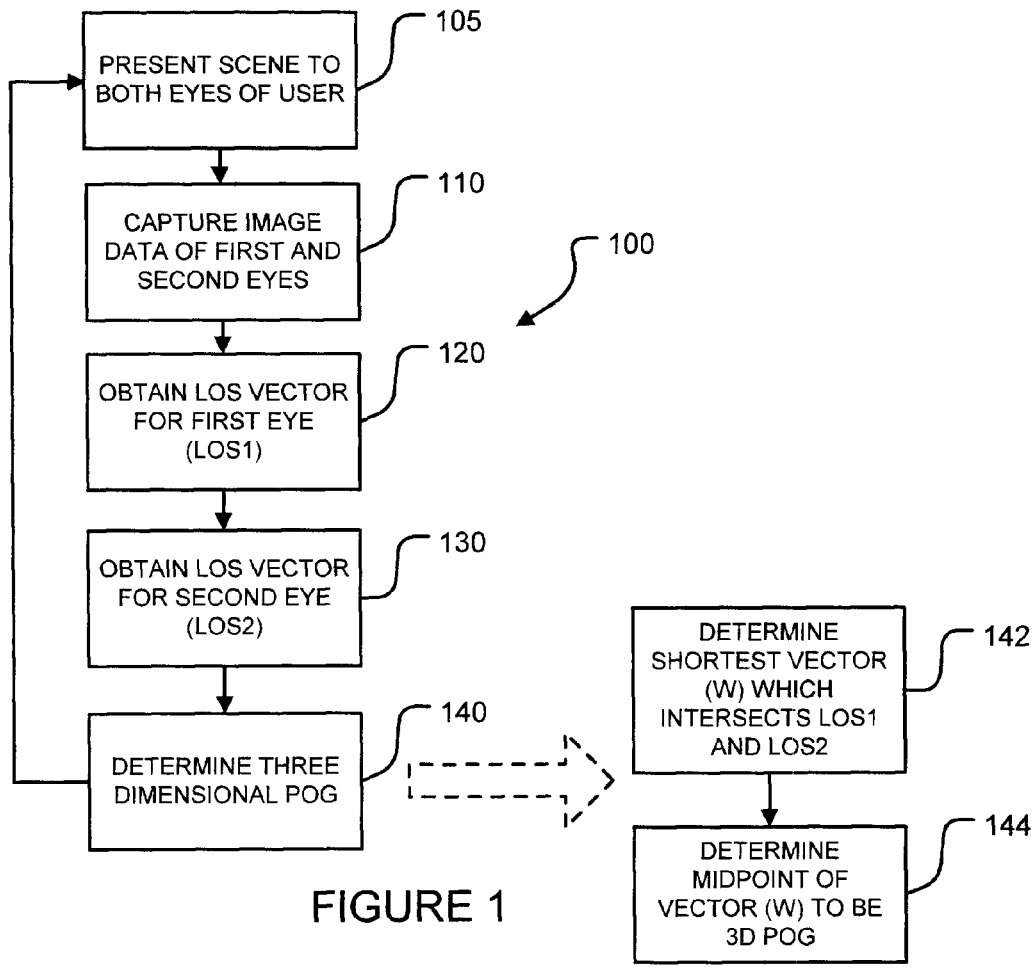
FIG. 1 schematically depicts a method for detecting a POG in three dimensions according to a particular embodiment of the invention.

FIG. 1 schematically depicts a method 100 for estimating the POG of a user in three dimensions according to a particular embodiment of the invention. Method 100 begins in block 105 which involves presenting a three-dimensional scene to both eyes of the user. The same single three-dimensional scene may be presented to both of the user's eyes. In some embodiments, the three-dimensional scene is the real world and there is no need to actively present the scene to both of the user's eyes as the user's eyes automatically take-in the real world scene. In other embodiments, the three-dimensional scene presented to both of the user's eyes is a three-dimensional scene created or otherwise generated by a scene generation system. By way of non-limiting example, a scene generation system may comprise: a 3D volumetric display, a holographic display, a parallax display or the like.

Block 110 involves capturing image data. The image data captured in block 110 comprises image(s) of both of the eyes of a user. The image data for each eye may be captured simultaneously or at different times. The image data for each eye may be captured using the same image-capturing device(s) or using separate image-capturing device(s) for each eye. Block 110 may also involve processing the image data such that the image data may be used to calculate LOS vectors for each of the user's eyes. A particular embodiment for capturing image data is explained in more detail below. In general, however, the capturing of image data in block 110 may be accomplished using any suitable image-capturing technique.

Once the image data is captured in block 110, method 100 proceeds to block 120 which involves using the block 110 image data to determine a LOS vector ($\overline{LOS}_1$) for a first of the user's eyes. The block 120 LOS vector $\overline{LOS}_1$ represents an estimate of the direction of the line-of-sight of a first one of the user's eyes and is based on one or more characteristics of the eye (e.g. position and/or orientation) ascertained from the block 110 image data. A particular embodiment for determining $\overline{LOS}_1$ is explained in more detail below. In general, however, determining the block 120 LOS vector $\overline{LOS}_1$ may be accomplished using a variety of suitable techniques. It is assumed that the block 120 LOS vector $\overline{LOS}_1$ originates from the center of the cornea of the user's first eye ($CC_1$). Block 120 may also involve estimating the location in space of the corneal center $CC_1$ of the user's first eye based on one or more characteristics of the eye ascertained from the block 110 image data.

Block 130 involves using the block 110 image data to determine a second LOS vector ($\overline{LOS}_2$) representing an estimate of the direction of the line-of-sight of a second one of the user's eyes based on characteristics of the eye ascertained from the block 110 image data. Block 130 may also involve determining a spatial location of the corneal center $CC_2$ of the user's second eye based on the block 110 image data. Block 130 may be similar to block 120, except that block 120 involves the second one of the user's eyes.

Figure 2:
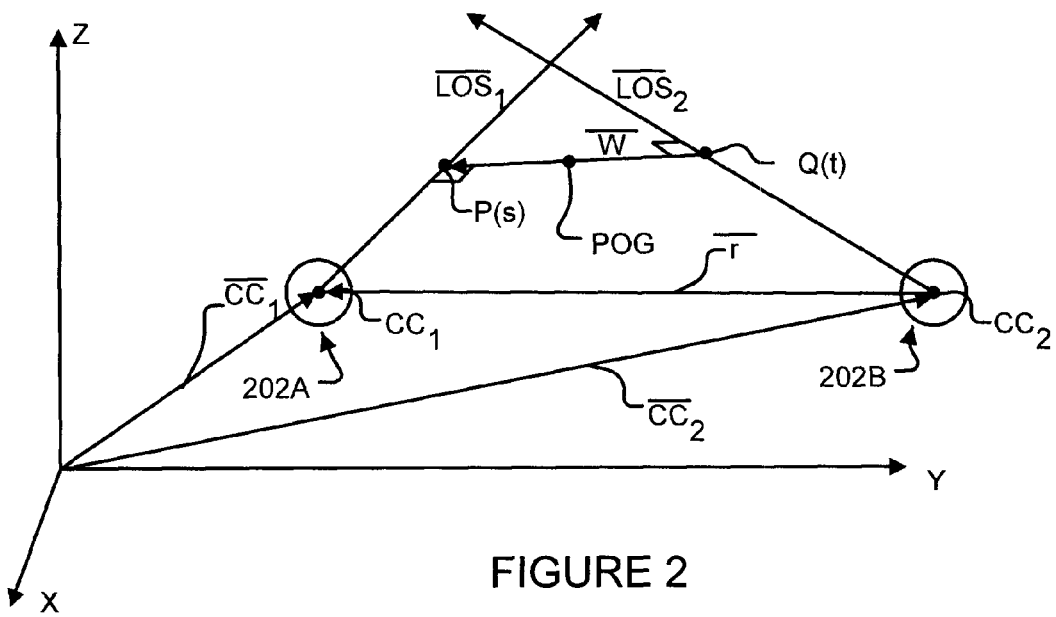
FIG. 2 is a schematic illustration of the geometry involved in the FIG. 1 method for using a pair of LOS vectors to determine a POG in three-dimensions.

After determining the LOS vectors $\overline{LOS}_1$, $\overline{LOS}_2$, method 100 proceeds to block 140 which involves determining the user's three-dimensional POG based on the LOS vectors $\overline{LOS}_1$, $\overline{LOS}_2$. FIG. 2 schematically depicts the geometry of the block 140 POG determination in accordance with a particular embodiment of the invention. As discussed above, blocks 120, 130 involve determining the LOS vectors $\overline{LOS}_1$, $\overline{LOS}_2$ and the corneal centers $CC_1$, $CC_2$ for each of the user's eyes 202A, 202B. In general, the LOS vectors $\overline{LOS}_1$, $\overline{LOS}_2$ may be extended as lines in three-dimensional space; however, the lines corresponding to LOS vectors $\overline{LOS}_1$, $\overline{LOS}_2$ will not necessarily intersect one another. That is, the lines corresponding to the LOS vectors $\overline{LOS}_1$, $\overline{LOS}_2$ may be skewed.

Blocks 142 and 144 schematically depict one possible embodiment for determining a three-dimensional POG using the LOS vectors $\overline{LOS}_1$, $\overline{LOS}_2$ and the corneal centers $CC_1$, $CC_2$ determined in blocks 120, 130. Block 142 involves determining a vector $\overline{W}$ which is the shortest possible vector that intersects the lines corresponding to both $\overline{LOS}_1$ and $\overline{LOS}_2$. By defining the vector $\overline{W}$ in this way, $\overline{W}$ will be orthogonal to both $\overline{LOS}_1$ and $\overline{LOS}_2$ or, equivalently:

$$\overline{LOS}_1 \cdot \overline{W} = \overline{LOS}_2 \cdot \overline{W} = 0 \tag{1}$$

where • represents the dot product operator.

The two points P(s) and Q(t) are defined to be the points at which $\overline{W}$ respectively intersects the lines extending from LOS vectors $\overline{LOS}_1$ and $\overline{LOS}_2$. Based on these definitions, it may be seen from FIG. 2 that:

$$\overline{W} = [P(s) - Q(t)] = [(\overline{CC}_1 + s\overline{LOS}_1) - (\overline{CC}_2 + t\overline{LOS}_2)] \tag{2}$$

where $\overline{CC}_1$ and $\overline{CC}_2$ are vectors between the origin and the locations of the corneal centers $CC_1$, $CC_2$ in three dimensions and s and t are unknown scaling parameters.

Substituting (2) into (1) yields a pair of equations in terms of the scaling parameters s, t:

$$s(\overline{LOS}_1 \cdot \overline{LOS}_1) - t(\overline{LOS}_1 \cdot \overline{LOS}_2) = \overline{LOS}_1 \cdot (\overline{CC}_2 - \overline{CC}_1) \tag{3}$$

$$s(\overline{LOS}_1 \cdot \overline{LOS}_2) - t(\overline{LOS}_2 \cdot \overline{LOS}_2) = \overline{LOS}_2 \cdot (\overline{CC}_2 - \overline{CC}_1) \tag{4}$$

With the exception of the scaling parameters s, t, the quantities in equations (3) and (4) are known from blocks 120 and 130. Block 142 may involve solving equations (3) and (4) (or equivalent equations) for the scaling parameters s and t and then using these scaling parameters s and t to compute $\overline{W}$ according to equation (2).

In the illustrated embodiment, block 144 involves determining the midpoint of the vector $\overline{W}$ to be the current estimate of the three-dimensional POG. After obtaining an estimate of the current POG in three-dimensions, method 100 may loop back to block 105, where the process may be repeated to continually track the user's POG in three dimensions.

Even where a human user's eyes are fixated at a POG in a three-dimensional scene (i.e. the POG is imaged onto the fovea of the user's eyes), the user's eyes exhibit a number of movements. Typically, a fixation lasts between from 200-600 ms and will encompass around 1° of visual angle. While fixating, the eye will drift with typical amplitudes on the order of 0.1° of visual angle and frequencies on the order of 2-5 Hz. This drift is typically compensated by microsaccades which are fast shifts in eye orientation with amplitudes on the same order as the amplitudes of the drift. Superimposed on the drift and the microsaccades are tremor movements, with typical amplitudes around 0.008° of visual angle and frequency components typically ranging from 30-150 Hz.

Without wishing to be bound by theory, it is thought that these small eye motions during fixation enable the sensors in the eye to be continually refreshed. The human brain subconsciously compensates for these small eye movements which occur during fixation. Consequently, humans are able to concentrate on a specific fixation without perceiving the small eye movements. However, these small eye movements can interfere with the precision or accuracy of LOS determination. The resultant inaccuracies can be compounded when a pair of LOS vectors are used to determine a three-dimensional POG. Consequently, it is desirable to include procedures in method 100 to accommodate these small eye movements while minimizing the impact on the three-dimensional POG determination.

In addition to these small eye movements which occur during fixation, the human eye exhibits saccades which are relatively large motions of the eye used to reorient the fovea to another area of interest. Saccades most offer range from 1°-40° of visual angle and last between 30-120 ms with a delay in a typical range of 100-200 ms between saccades. During saccades, both of a user's eyes do not necessarily move in unison and the sensitivity of both eyes to visual input may be reduced. Furthermore, for the brain to register a true conscious POG, the scene which includes the POG is focused on the retina of the user's eye. The process by which the ciliary muscles compress or expand the lens in the eye to change its focal depth is referred to as accommodation. In many applications, it is not desirable to estimate a POG (or at least to use POG estimation information) during saccades, as such POG estimations do not correspond to conscious POG positions in the user's brain.

Further to all of the movements of the user's eyes, the user may move his or her body and more particularly, his or her head. Head movements can make it difficult to determine the LOS of the user's eyes. These difficulties can be exacerbated when a pair of LOS vectors are used to determine a user's POG in three dimensions. Consequently, it is desirable to include procedures in method 100 to accommodate these head movements while minimizing the impact on the three-dimensional POG determination.

Figure 3:
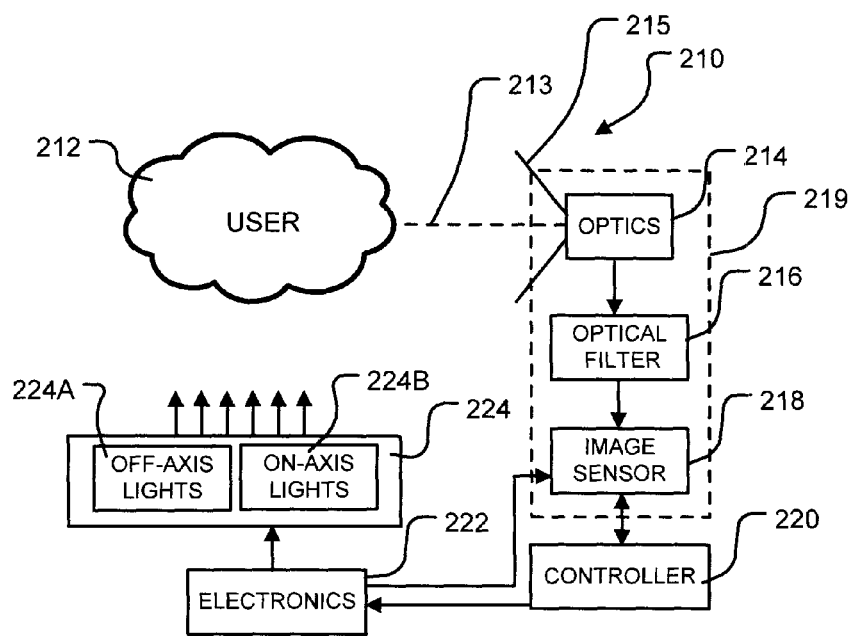
FIG. 3 is a schematic diagram of a system for performing the method of FIG. 1 in accordance with a particular embodiment of the invention.

FIG. 3 schematically depicts an apparatus 210 for estimating the POG of a user in three dimensions according to a particular embodiment of the invention. FIG. 3 shows that apparatus 210 comprises an imaging system 219 that is located, or otherwise configured, to view a user 212 (or at least his or her eyes). In the illustrated embodiment, imaging system 219 includes optics 214 (which may comprise one or more lenses and/or mirrors), an optical filter 216 and an image sensor 218. Imaging system 219 has an optical axis 213 and a field of view 215. Although the user is permitted to have head movement, the user's head is preferably oriented such that his or her eyes are in the field of view 215 of imaging system 219. In some embodiments, apparatus 210 may include a plurality of imaging systems 219 so as to view user 212 from multiple locations. The use of a plurality of imaging systems 219 facilitates a combined field of view which can permit user 212 to have a wider range of motion. The fields of view 215 of these imaging systems 219 may be overlapping or non-overlapping. In some embodiments, the inclusion of multiple imaging systems 219 may be used to capture images of each of the user's eyes separately.

In general, it is desirable for image sensor 218 to have a relatively high resolution and a relatively high frame rate, provided that controller 220 is able to accommodate such resolution and frame rate as described below. Increases in resolution of image sensor 218 allow apparatus 210 to accommodate a larger range of head motion with the user's eyes remaining in the field of view of sensor 218 while still outputting image data with sufficient spatial resolution to accurately determine the LOS vectors of the user's eyes as discussed in more detail below. The resolution of image sensor 218 may (but need not necessarily) be on the order of 640× 480 pixels or greater. Increases in the frame rate of image sensor 218 allow apparatus 210 to accommodate faster head and eye movement without losing LOS tracking of the user's eyes. The frame rate of image sensor 218 may (but need not necessarily) be on the order of 30 Hz or greater. In some embodiments, image sensor 218 may be implemented by a camera which may include its own control components and/or I/O components (not explicitly shown). Image sensor 218 may (but need not necessarily) be digital.

Apparatus 210 incorporates optics 214. Optics 214 may comprise one or more lenses, mirrors and/or other optical components. Optics 214 be adjusted depending on the relative location of the eyes of user 212. Optics 214 may be used in some applications to adjust the image of user 212 which reaches image sensor 218. In some applications, optics 214 may be controlled by imaging system 219 and/or control components associated with imaging system 219.

Apparatus 210 incorporates lighting 224 for illuminating user 212. In currently preferred embodiments, lighting 224 operates at infrared (IR) wavelengths (e.g. 800 nm-1000 nm). Light at these wavelengths is invisible and therefore does not distract user 212. In addition, fluorescent lights, which form the ambient light sources in the current development environment, exhibit low light intensities in this spectral range. Consequently, the performance of apparatus 210 can be made relatively insensitive to ambient light effects by including optional optical filter 216 which passes IR light, but which blocks light in the visible spectrum. In general, lighting 224 may operate at other wavelengths and optical filter 216 may be selected to pass light at the wavelength of lighting 224 and to attenuate light at other wavelengths. In one particular embodiment, lighting 224 comprises a plurality of LEDs which produce light at approximately 880 nm. Groups of such LEDs may be closely packed together to approximate point light sources.

In some embodiments, the physical arrangement of lights in lighting 224 (not explicitly shown in FIG. 3) can be used to help extract the features of interest from within the image data captured by imaging system 219. More particularly, one or more LEDs in lighting 224 may be placed off of the optical axis 213 of imaging system 219 to provide off-axis lighting 224A and one or more LEDs in lighting 224 may be placed as close as reasonably possible to optical axis 213 to provide on-axis lighting 224B. For the sake of clarity only, in the schematic illustration of FIG. 3, off-axis lighting 224A and on-axis lighting 224B are not shown in their actual positions relative to imaging system 219. In one particular embodiment, off-axis lighting 224A is provided by a plurality of groups of LEDs spaced apart (circumferentially or otherwise) around optical axis 213 and on-axis lighting 224B is provided by a plurality of LEDs placed as close as reasonably possible to optical axis 213. Each spaced-apart group of off-axis LEDs may include one or more individual LEDs depending on illumination requirements.

Figure 16:
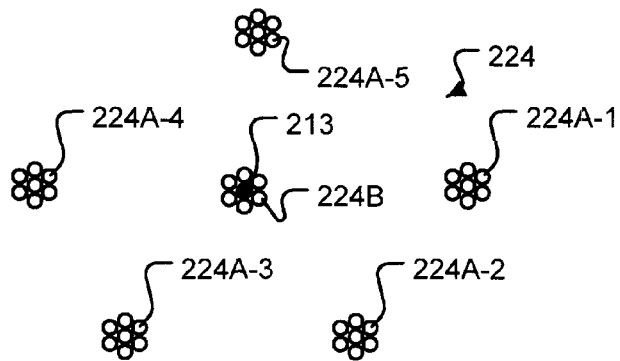
FIG. 16 schematically depicts an arrangement of lighting suitable for use with the FIG. 3 system according to one particular exemplary embodiment of the invention.

FIG. 16 schematically depicts an arrangement of lighting 224 according to one particular exemplary embodiment. As discussed above, off-axis lights 224A are located away from optical axis 213 and may comprise a plurality of groups of LEDs (or other light source(s)) which approximate point sources. In the illustrated embodiment of FIG. 16, off-axis lights 224A comprise five groups of LEDs which approximate five corresponding point source approximations 224A-1, 224A-2, 224A-3, 224A-4, 224A-5. Point source approximations 224A-1, 224A-2, 224A-3, 224A-4, 224A-5 may be collectively and individually referred to herein as off-axis lights 224A. In general, there may be a different number of off-axis lights 224A, although two or more off-axis lights 224A are required for LOS vector calculation according to the model-based method described herein and three or more off-axis lights 224A may be used to provide redundancy against the loss or corruption of off-axis glints due to eye movement, as described in more detail below. In the illustrated embodiment, on axis lights 224B comprise a group of LEDs (or other light source(s)) which are located at or near optical axis 213.

In the illustrated embodiment, off-axis lights 224A and on-axis lights 224B are provided by groups of LEDs and each group comprises a plurality of light sources. This is not necessary, each group may contain light sources other than LEDs and may contain a single light source. In some embodiments, apparatus 210 may comprises multiple sets of lighting 224, off-axis lights 224A and/or on-axis lights 224B. In some embodiments, there may be a one-to-one correspondence between lighting 224 and imaging systems 219 (i.e. one set of lighting 224 for each imaging system). In other embodiments, there may be multiple lighting systems 224 to service a single imaging system 219. In still other embodiments, each imaging system 219 may comprise its own corresponding on-axis lighting 224B and multiple imaging systems 219 may share the same off-axis lighting 224A.

Due the retro-reflectivity of the user's retina, on-axis light 224B that enters the eye and strikes the retina is typically reflected back toward imaging system 219 on or near optical axis 213 and results in images where the user's pupil appears relatively bright. Images obtained using only on-axis components 224B of lighting 224 may be referred to as "bright pupil" images. Images obtained using only the off-axis components 224A of lighting 224 are not retro-reflected along optical axis 213 and therefore do not illuminate the user's pupil in the same manner. Images obtained using only the off-axis components 224A of lighting 224 may be referred to as "dark pupil" images. Off-axis lights 224A result in Purkinje reflections (more commonly referred to as "glints") from the corneal surface which appear in the resultant dark pupil images. In particular embodiments, obtaining dark pupil images involves activating any two or more of the groups of off-axis lights 224A to obtain two or more corresponding glints. The particular groups of off-axis lights 224A selected may depend on the quality of glints that they produce. As explained in more detail below, the bright pupil and dark pupil images can be used to help distinguish the user's pupil from the user's iris within the captured images and can help to locate glints within the captured images.

Apparatus 210 is controlled by controller 220. Controller 220 may comprise one or more programmable processor(s) which may include, without limitation, embedded microprocessors, computers, groups of data processors or the like.

Some functions of controller 220 may be implemented in software, while others may be implemented with specific hardware devices. The operation of controller 220 may be governed by appropriate firmware/code residing and executing therein, as is well known in the art. Controller 220 may comprise memory or have access to external memory. In one particular embodiment, controller 220 is embodied by a computer, although this is not necessary, as controller 220 may be implemented in an embedded architecture or some other control unit specific to apparatus 210. Controller 220 may comprise or may otherwise be connected to other interface components (not explicitly shown) which may be used to interact with any of the other components of apparatus 210. Such interface components will be understood by those skilled in the art.

In the illustrated embodiment, apparatus includes electronics 222 which are used by controller 220 to synchronize the operation of imaging system 218 and lighting 224 and, in some embodiments, to control which of off-axis lights 224A are active. Synchronization of image sensor 218 and lighting 224 may involve alternatively: activating one or more off-axis lights 224A and activating imaging system 218 for a period of time in which off-axis lights 224A are activated to capture a dark pupil image; and activating one or more on-axis lights 224B and activating image sensor 218 for a period of time in which on-axis lights 22B are activated to capture a bright pupil image. In particular embodiments, the activation of image sensor 218 may be controlled by a shutter or the like (not explicitly shown).

Particular embodiments of the functional blocks of method 100 are now described in more detail. Operational details of processes similar to the functional operation of some of the method 100 processes are described for one eye in C. Hennessey, "Eye-gaze tracking with free head motion," Master's thesis, University of British Columbia, August 2005 (Hennessey), which is hereby incorporated herein by reference and which is hereinafter referred to as "Hennessey".

Figure 4:
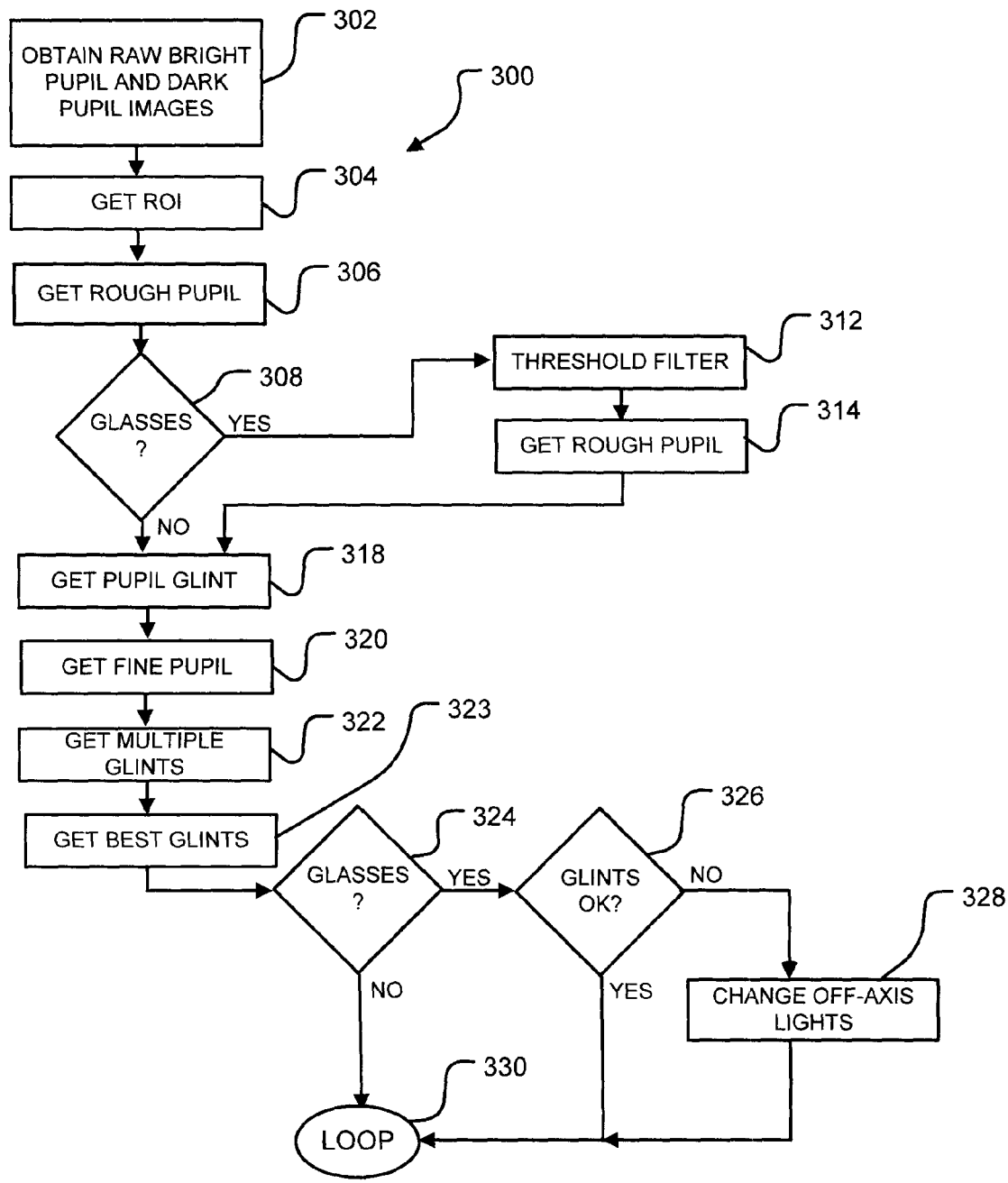
FIG. 4 schematically depicts a particular embodiment of a method for obtaining image data containing image(s) of the user's eyes and extracting, from the image data, a number of characteristics which may be used to determine the LOS vectors used in the method of FIG. 1.

As discussed above, block 110 involves capturing image data for the user's first and second eyes. A particular embodiment of a method 300 for capturing this image data is depicted in FIG. 4. Method 300 begins in block 302 which involves capturing raw image data that includes a bright pupil image and a dark pupil image for each eye. In particular embodiments, both eyes are captured in a single image. That is, a single block 302 bright pupil image contains bright pupil images of both eyes and a single block 302 dark pupil image contains dark pupil images of both eyes. Simultaneous capture of the bright pupil and dark pupil images for both eyes avoids inter-image disparity that may lead to spurious results for the LOS and POG estimates. However, simultaneous capture of the bright pupil image for both eyes and the dark pupil image for both eyes is not necessary. In some embodiments, bright pupil and dark pupil images may be obtained separately for each eye.

The raw images obtained in block 302 may include all of the data recorded by image sensor 218 (FIG. 3). In the first iteration of method 300 or when the user exhibits substantial head movement, it may be desirable to use the entirety of the recorded image data. In subsequent iterations, however, it is desirable to reduce the amount of block 302 image data used in the remainder of method 300, since this will improve the looping speed of method 100 (FIG. 1). On the second and subsequent iterations of method 300, the block 302 image data recorded by image sensor 218 is reduced to a portion of the image data recorded in block 304. The block 304 portion of image data may be referred to as a "region of interest" (ROI) and particular block 304 ROIs may be ascertained from the centers of the user's pupils. As discussed in more detail below, the centers of the user's pupils may be determined in a previous iteration of method 100.

Figure 5:
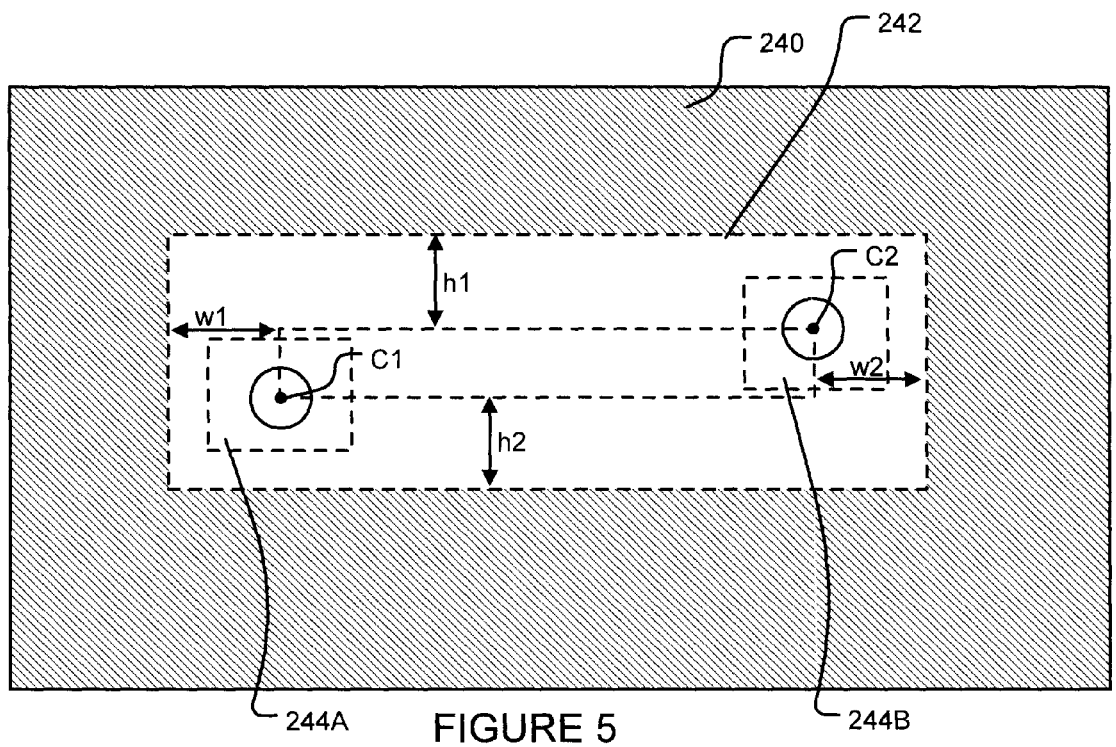
FIG. 5 is an example of regions of interest within the image data that are suitable for use with the method of FIG. 4.

Particular examples of suitable ROIs are shown in FIG. 5. In the FIG. 5 example, the entire image captured by image sensor 218 is shown schematically as the hashed region 240 and the centers of the user's pupils (within image 240) determined in the previous iteration of method 100 are shown as $C_1$ and $C_2$. In one of the FIG. 5 embodiments, the block 304 ROI 242 is determined to include image data that is: spaced apart from the uppermost pupil center ($C_2$ in the illustrated example) by a distance $h_1$; spaced apart from the rightmost pupil center ($C_2$ in the illustrated example) by a distance $w_2$; spaced apart from the bottommost pupil center ($C_1$ in the illustrated example) by a distance $h_2$; and spaced apart from the leftmost pupil center ($C_1$ in the illustrated example) by a distance $w_1$. In some embodiments, $h_1=h_2$ and $w_1=w_2$. In some embodiments, $w_1$ and $w_2$ need not be used and ROI 242 may include the entire width of the image data captured by image sensor 218.

In the other FIG. 5 embodiment, the block 304 ROI 244A, 244B (collectively 244) is determined to include a first region 244A surrounding the first pupil center $C_1$ and a second region 244B surrounding the second pupil center $C_2$. In the illustrated embodiment, regions 244A, 244B are rectangles centered at $C_1$ and $C_2$. However, this is not necessary. In other embodiments, regions 244A, 244B may have other shapes, such as circular shapes, for example, and need not be centered on pupil centers $C_1$, $C_2$. The block 304 process of obtaining a ROI may be implemented in hardware and/or software. In some embodiments, imaging system 219 (FIG. 3) may determine the ROI (at least in part) prior to outputting the image data (i.e. blocks 302 and 304 of method 300 may be performed together by imaging system 219). In other embodiments, controller 220 (FIG. 3) may comprise or have access to software which determines the ROI (at least in part) on the basis of some or all of the image data captured by imaging system 219. In some embodiments, a first ROI (e.g. ROI 242) may be implemented in hardware and a second ROI (e.g. ROI 244) may be implemented in software. In some embodiments, depending on processing power, a ROI is not required, and block 304 may be skipped.

In the remaining discussion of method 300 (FIG. 4), it is assumed that references to image data refer to the subsets of image data obtained by the block 304 ROI process. In addition, while not explicitly shown, subsequent processing in method 300 is performed on the image data for each of the user's eyes. The method 300 data extracted for each eye are used to estimate the LOS for each of the user's eyes as discussed in more detail below.

Referring again to FIG. 4, block 306 involves obtaining approximate pupil characteristics (referred to herein as the "rough pupil"). A method 350 for the block 306 rough pupil extraction according to a particular embodiment of the invention is shown in FIG. 6. Method 350 begins in optional block 352, which involves applying a smoothing filter (e.g. a Gaussian filter) to the bright pupil and dark pupil image data to smooth the image data and to reduce image noise. Block 354 involves subtracting the dark pupil image from the bright pupil image (i.e. the intensities of the pixels of the dark pupil image from the intensities of corresponding pixels of the bright pupil image) to produce a difference image. The difference image highlights the pupil (which is bright in the bright pupil image due to on-axis lights 224B and dark in the dark pupil image) and helps to segment the pupil from the iris.

Block 356 involves separating the pixels corresponding to the relatively bright pupil from the pixels corresponding to the relatively dark background in the difference image. In particular embodiments, the block 356 pupil pixel separation involves creating a bimodal intensity/brightness level histogram using the difference image, wherein the first mode of the histogram reflects the dark background and the second mode of the histogram reflects the bright pupil. A thresholding process may then be used to make a binary separation of the pixels corresponding to the relatively bright pupil mode from the pixels corresponding to the relatively dark background mode. For example, pixels of the difference image which are within a threshold intensity region (e.g. determined from the second mode of the histogram) may be determined to be part of the pupil and may be assigned a binary value (e.g. 1) and pixels outside of this threshold intensity region may be determined to not be part of the pupil and maybe assigned a different binary value (e.g. 0).

Block 358 involves determining a pupil contour. The largest contour remaining after the binary thresholding process of block 356 is likely to be the pupil. In one embodiment, block 358 involves identifying the contour with the largest number of pixels that is within a shape that corresponds with known pupil characteristics. Such a shape may be an elliptical shape, for example, and the pupil characteristics may be a ratio of the major ellipse axis to the minor ellipse axis that is relatively close to unity (i.e. an elliptical shape that is somewhat close to circular). A rejection test may be performed in block 358 to reject contours that do not qualify as pupils. In some embodiments, this rejection test may involve computation of an isoperimetric quotient. For example, an isoperimetric quotient Q may be defined as $$Q = \frac{4\pi A}{p^2}$$

where A is the area of the contour and p is the perimeter of the contour. The quotient Q is equal to unity for a circle and decreases for objects with a larger perimeter to area ratio. A threshold (e.g. Q=0.8) may be set such that if Q is less than the threshold, the contour is rejected. In another example, an ellipsoidal thresholding test may be constructed wherein the width and height of the contour must be within threshold windows for the contour to qualify. Although not explicitly shown in FIG. 4 or 6, if the detected pupil is rejected in block 358 (i.e. the detected pupil fails the rejection test), then image processing algorithm 300 may exit and return to block 302 to obtain further image data. Block 360 involves applying an ellipse fitting algorithm to boundary points of the block 358 pupil contour. In particular embodiments, the block 360 ellipse fitting technique involves a least squares optimization. In other embodiments, the block 360 ellipse fitting algorithm may comprise some other suitable curve fitting technique. The center of the block 360 ellipse equation may be used as the center of the pupil for further processing and for subsequent iterations of method 300.

Returning to method 300 (FIG. 4), block 308 involves an inquiry into whether glasses have been detected. Eyeglasses generate bright reflections which may interfere with the pupil identification process. Block 308 may involve comparing the average intensity of the pupil pixels in the bright pupil image with a threshold brightness level. Reflections from eyeglasses are typically brighter than reflections from the retina. If the average intensity of the bright pupil image pixels determined in block 306 to be part of the "pupil" is above this threshold brightness level, then it may be concluded (block 308 YES output) that this "pupil" is actually a reflection from eye glasses rather than a true pupil. If on the other hand the average intensity of the bright pupil image pixels determined in block 306 to be part of the pupil is below this threshold brightness level, then it may be concluded (block 308 NO output) that glasses have not adversely impacted the block 306 rough pupil detection.

If it is concluded in block 308 that the user is wearing glasses (block 308 YES output), then method 300 proceeds to block 312 which involves determining which pixels in the bright pupil image have intensity values higher than the block 308 threshold and setting the intensity values of these pixels to zero. Method 300 then proceeds to block 314 to obtain another set of rough pupil characteristics. Block 314 may be substantially similar to the block 306 process for obtaining the rough pupil characteristics, except that the image data has been altered by removal of the high intensity pixels reflected from the glasses from the bright pupil image.

As discussed above, where valid rough pupil characteristics are not determined (e.g. in block 308 or block 314), then method 300 may return to block 302 to obtain more image data. Where method 300 exits and returns to block 302 prior to completing on a number of subsequent iterations (e.g. due to invalid rough pupil characteristics), controller 220 may cause method 300 to operate using the entire images captured by image sensor 218 (rather than the images as reduced by the block 304 ROI process). This may help to resolve the issue of an eye moving outside of the ROI.

After obtaining valid rough pupil characteristics (in block 308 or block 314), method 300 proceeds to block 318. Block 318 involves obtaining pupil glint information from the bright pupil image. This pupil glint information can be used to refine the detected pupil characteristics in block 320 as explained in more detail below. FIG. 7 depicts a method 370 for the block 318 process of extracting pupil glint information from the bright pupil image in accordance with a particular embodiment of the invention. As discussed above, the bright pupil image is obtained using on-axis lights 224B. On-axis lights 22B create a corresponding glint (i.e. corneal reflection of on-axis lights 224B) in the bright pupil image. In general, method 370 for extracting the pupil glint from the bright pupil image is based on the realization that the glint created by on-axis lights 224B represents the brightest intensity pixels in the bright pupil image.

Method 370 commences in block 372, where a mask is applied to the bright pupil image data to reduce the possibility of mistakenly interpreting a glint located on the sclera (i.e. rather than the cornea). In one particular embodiment, the block 372 mask is centered at the center of the rough pupil (as determined in block 306 or 314 as the case may be) and may be circular or some other suitable shape. The dimensions of the block 372 mask may be selected such that the mask is roughly the size of the user's iris. These dimensions may be selected based on known population averages or may be measured on a per user basis, for example. After applying the block 372 mask, block 374 involves locating the pixel having the highest intensity value in the resultant masked bright pupil image data. The block 374 pixel detection may involve a maximum function operating on the pixel intensity values.

Block 376 involves computing an average intensity of the block 374 highest intensity pixel and pixels surrounding the block 374 highest intensity pixel. In one particular embodiment, the pixels selected for the block 376 intensity average include the block 374 highest intensity pixel and the eight pixels immediately surrounding the block 374 highest intensity pixel. These eight surrounding pixels may include the two horizontal neighbors of the highest intensity pixel, the two vertical neighbors of the highest intensity pixel and the four diagonal neighbors of the highest intensity pixel. In other embodiments, other groups of pixels in a vicinity of the block 374 highest intensity pixel may be selected for the block 376 averaging process. Block 378 involves determining a threshold intensity value on the basis of the block 376 average calculation. The block 378 threshold intensity value may be less than the block 376 average by an experimentally determined percentage. This threshold intensity is then applied to the masked bright pupil image data, resulting in a binarized image which distinguishes pixels having intensities above the block 378 threshold and pixels having intensities below the block 378 threshold. Pixels having intensities above the block 378 threshold are determined to be part of the bright pupil glint.

Block 380 then involves determining which contour in the resultant binary image is the bright pupil glint. The block 380 process may involve searching all of the contours in the binary image to locate a shape that meets a range of expected sizes for the bright pupil glint. In block 382, an ellipse is then fit to the block 380 glint contour. This ellipse fitting may be similar to the ellipse fitting in block 360. The center of the fitted ellipse may be determined to be the center of the bright pupil glint for the purposes of further processing.

Returning to method 300 (FIG. 4), after determining the bright pupil glint in block 318, method 300 uses the bright pupil glint to determine fine pupil characteristics in block 320. The block 320 fine pupil characteristics may involve obtaining an increased accuracy determination of the block 306 rough pupil characteristics. FIG. 8 depicts a method 400 for determining the block 320 fine pupil information according to a particular embodiment of the invention. The method 400 technique extracts the fine pupil characteristics from the bright pupil image. Method 400 begins in block 402 which involves obtaining rough pupil information (determined in block 306 or 314) and pupil glint characteristics (determined in block 318). This information obtained in block 402 may be used to provide masks in the subsequent procedures of method 400. In particular embodiments, the block 306/314 rough pupil obtained in block 402 may be the binarized rough pupil image obtained in block 356 and the pupil glint obtained in block 402 may be the binarized pupil glint image obtained after the block 378 thresholding process.

In block 404, the block 318 pupil glint is expanded or dilated. As explained in more detail below, the dilation of the block 318 pupil glint ensures that the mask removes all of the pupil glint from the bright pupil image. In some embodiments, block 404 is not necessary. The presence of the block 404 dilation and the amount of dilation used in block 404 may be dependent on the pixels used for the block 376 averaging process and/or the threshold used in the block 378 thresholding process to determine the block 318 pupil glint. Block 406 involves inverting the binarized pixel values of the pupil glint (as optionally dilated in block 404). In block 408, the result of the block 406 pupil glint inversion is logically ANDed with the binarized rough pupil image to produce a mask. The effect of the block 408 AND operation is to remove the pixels corresponding to the bright pupil glint from the binarized rough pupil image.

The block 408 binary mask has a certain binary value (e.g. 1) in the pixels corresponding to the rough pupil, except for those pixels in the block 318 bright pupil glint (as optionally dilated in block 404) which have the opposing binary value (e.g. 0). The pixels outside the rough pupil also have the opposing binary value (e.g. 0) in the block 408 mask.

Block 410 involves applying the block 408 mask to the original bright pupil image (after the above-described ROI operations, if present). The result of the block 410 masking process is an image where: (i) the pixels inside the block 408 mask (e.g. the pixels in the rough pupil but not including those pixels in the bright pupil glint (as optionally dilated in block 404)) have intensity levels corresponding to those captured in the bright pupil image of block 302; and (ii) the pixels outside the block 408 mask (e.g. the pixels in the bright pupil glint (as optionally dilated in block 404) and the pixels outside of the rough pupil) have their intensity levels reduced to zero. The result of the block 410 masking process may be referred to as the "masked bright pupil image".

Block 412 involves computing the average of the intensity levels of the pixels in the masked bright pupil image. This average represents the average intensity of pixels that are in the rough pupil, but which are not part of the high-intensity glint corresponding to on-axis lights 224B. The block 412 average is used as the basis for determining a threshold level to be used in the subsequent procedures of method 400. Block 412 may involve reducing this average value by an experimentally determined percentage or an experimentally determined offset to determine the threshold level. In other embodiments, the block 412 threshold value may be based on some other function of the average of the intensity level of the pixels in the masked bright pupil image.

The block 412 threshold is applied to the unmasked bright pupil image in block 414 to provide a binarized output. Pixels in the unmasked bright pupil image having intensity levels higher than the block 412 threshold are assigned one binary value (e.g. 1) and pixels in the unmasked bright pupil image having intensity levels less than or equal to the block 412 threshold are assigned the opposing binary value (e.g. 0). Pixels corresponding to the pupil glint in the bright pupil image typically have intensity values greater than those of the block 412 threshold and will therefore be included in the resultant block 414 binarized bright pupil image.

Block 415 involves finding the boundary of the block 414 binarized bright pupil image and setting the intensity values of those boundary pixels to one binary value (e.g. 1) and setting all of the other pixels to the opposing binary value (e.g. 0). The result of block 415 is typically a binary outline of the pupil overlapped in part by a binary outline of the bright pupil glint. In block 416, the resultant block 415 binary outline is logically ANDed with the block 406 inverted pupil glint to remove the glint from the block 415 binary outline. The result of block 416 is a binary image having pixels with a first binary value (e.g. 1) on a portion of the outline of the pupil and the opposing binary value (e.g. 0) in most other locations. This portion of the outline of the pupil may be referred to as the "fine pupil contour".

The block 416 binary image may have some spurious pixels that are not truly on the fine pupil contour. Such spurious pixels may be generated by noise or the like. Block 418 involves identifying the fine pupil contour within the binary image resulting from block 416. In one particular embodiment, block 418 involves fitting a bounding box to each contour in the block 416 binary image and then determining the distance between the center of each bounding box and the center of the rough pupil ellipse (as determined in block 360). The contour whose bounding box center is most proximate to the center of the rough pupil ellipse is then identified as the fine pupil contour.

Block 422 involves fitting an ellipse to the fine pupil contour. The block 422 ellipse fitting may be similar to the ellipse fitting performed in block 360 described above. The block 422 ellipse may be used to determine the LOS of the corresponding eye as discussed in more detail below.

Returning to method 300 (FIG. 4), after determining the fine pupil characteristics in block 320, method 300 proceeds to block 322 which involves determining the characteristics of two or more off-axis glints from the dark pupil image. The block 322 off-axis glints may be created by corneal reflection of off-axis lights 224A (see FIGS. 3 and 16) which, as discussed above, may be configured to approximate point sources at locations away from optical axis 213. The characteristics of these off-axis glints may be used to calculate the LOS of the corresponding eye as discussed in more detail below. The block 322 procedure for determining the characteristics of the off-axis glints from the dark pupil image is similar in many respects to method 370 described above for detecting the pupil glint from the bright pupil image.

The block 322 procedure for determining the characteristics of two or more off-axis glints from the dark pupil image may differ from method 370 in that the block 378 thresholding process is likely to reveal a binarized image having a plurality of glint candidates corresponding to the plurality of off-axis lights 224A (see FIGS. 3 and 16) which are used to form the dark pupil image. Ellipses may be fit to each of the pair of glint candidates to determine their shapes and center locations in a procedure similar to that of block 382 discussed above.

Method 300 then proceeds to block 323 which involves mapping the block 322 off-axis glints to their corresponding off-axis light sources 224A (see FIGS. 3 and 16). For the model-based method of calculating the LOS vectors (described below), it is desirable to have at least two off-axis glints to facilitate triangulation of the cornea center CC in three-dimensions. However, the block 322 off-axis glints may be distorted or lost due to movement of the eye and/or movement of other body parts (e.g. head or neck) which result in movement of the eye. For example, the block 322 off-axis glints may be distorted or lost when the images of off-axis lights 224A are located off the cornea (e.g. on the sclera) or even at or near the boundary between the cornea and the sclera. To provide redundancy (i.e. to make it more likely that the images of at least two off-axis lights 224A will be present on the cornea), off-axis lights 224A may be arranged to provide three or more distinct off-axis point source approximations (see point source approximations 224A-1, 224A-2, 224A-3, 224A-4, 224A-5 of FIG. 16) which result in three or more corresponding off-axis glints.

Block 323 involves mapping the individual off-axis glints detected in block 322 to the individual off-axis lights 224A. The block 323 mapping is desirable for determining the LOS vectors according to the model-based technique described below. In embodiments which use only two off-axis lights 224A, the block 323 mapping may be relatively simple and may involve comparing the x and y pixel displacements of the block 322 off-axis glints. However, in embodiments where the number of off-axis lights 224A is three or more to provide redundancy against the loss or corruption of the off-axis glints, the block 323 mapping may be more complex.

Figures 17A, 17B:
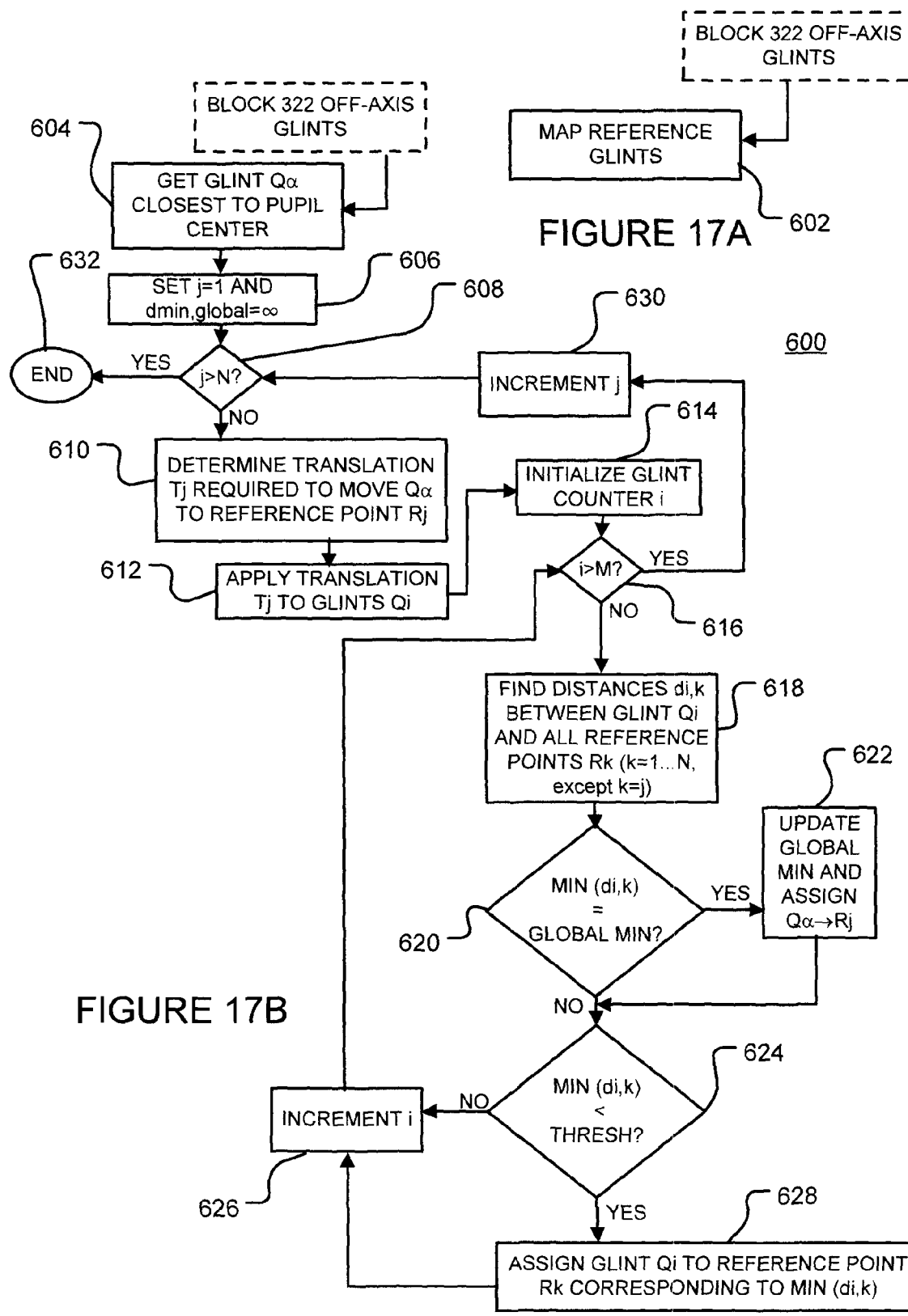
FIGS. 17A and 17B schematically illustrate a method for mapping detected off-axis glints to corresponding off-axis lights according to a particular embodiment of the invention.

In one particular embodiment, the block 323 mapping between off-axis glints and off-axis light sources 224A may be performed using a pattern matching technique which attempts to match the block 322 off-axis glints $Q_i$ (i=1 . . . M) obtained in each iteration of method 300 to a set of reference glints $R_j$ (j=1 . . . N), for which the correspondence between reference glints $R_j$ and off-axis light sources 224A is known. FIGS. 17A and 17B schematically depict a pattern matching method 600 which may be used to match off-axis glints $Q_i$ (i=1 . . . M) to a set of reference glints $R_j$ (j=1 . . . N) according to a particular embodiment of the invention.

Figure 18A:
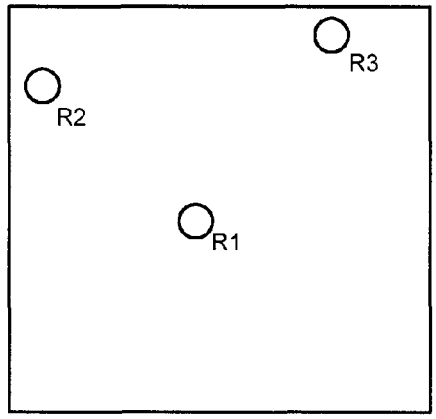
FIGS. 18A-18E schematically depict reference points and detected glints in the various iterations of the FIG. 17B mapping method.

Pattern matching method 600 shown in FIGS. 17A and 17B involves obtaining a reference glint pattern which includes glint data (e.g. glint locations) for a set of N valid reference glints $R_j$ (j=1 . . . N) and mapping the individual reference glints $R_j$ to their corresponding off-axis light sources 224A. In the illustrated embodiment, this reference glint pattern $R_j$ (j=1 . . . N) is obtained and mapped in block 602 of FIG. 17A. An exemplary reference glint pattern $R_j$ (j=1 . . . N) is shown schematically in FIG. 18A. In the illustrated example, N=3 and there are three reference glints $R_1$, $R_2$ and $R_3$.

Obtaining and mapping a reference glint pattern $R_j$ (j=1 . . . N) in block 602 may be performed in a first iteration of method 300 (FIG. 4) or in a different calibration iteration, for example. A user may be asked to position their head and/or to focus on a particular point (e.g. a central point) during the block 602 calibration. With the user's head and eyes oriented in a particular manner (i.e. configured for calibration), the block 602 mapping between reference glints $R_j$ and their corresponding off-axis lights 224A may be performed manually based on user knowledge of the locations of off-axis lights 224A and the corresponding reference glints $R_j$. In some embodiments, the block 602 mapping between reference glints $R_j$ and their corresponding off-axis lights 224A may be automated based on relationships between the locations of off-axis lights 224A to corresponding reference glints $R_j$ when the user's head and eyes are configured for calibration. By way of non-limiting example, if the head is configured for calibration in block 602 such that all glints are detected (segmented from the image) properly then the reference glints $R_j$ can be mapped to off-axis lights 224A based on spatial relationships between the reference glints $R_j$ and off-axis lights 224A (i.e. the glint to the left is the left light source, glint to the right is right light source, top most glint is the top most light source, etc.)

After obtaining the reference glint pattern $R_j$ (j=1 . . . N) and mapping the individual glints $R_j$ to corresponding off-axis lights 224A in block 602, subsequent iterations of method 600 involve a pattern matching method which matches a pattern of off-axis glints $Q_i$ (i=1 . . . M) obtained in block 322 (FIG. 4) to the reference glint pattern $R_j$ (j=1 . . . N) and thereby maps each of the detected off-axis glints $Q_i$ to a corresponding off-axis light 224A. This pattern matching method is schematically depicted in FIG. 17B.

Figure 18B:
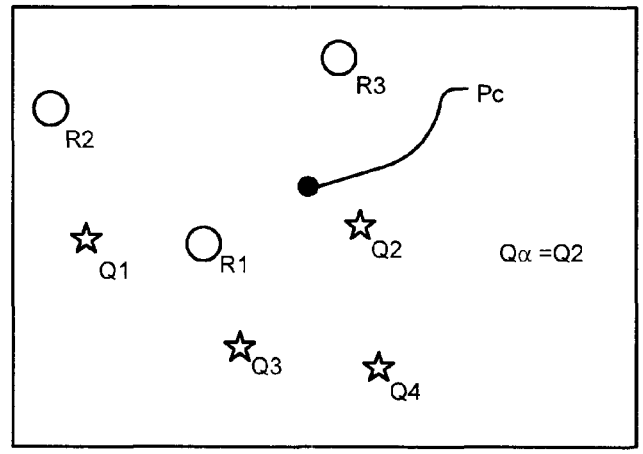

The FIG. 17B pattern matching method begins in block 604 which involves getting the off-axis glints $Q_i$ (i=1 . . . M) obtained in block 322 (FIG. 4) and determining which particular glint $Q_\alpha$ is closest to the image pupil center ($p_c$). A particular exemplary illustration of the block 604 process is shown schematically in FIG. 18B, where the block 322 process has detected M=4 glints, $Q_1, Q_2, Q_3, Q_4$. The image pupil center $p_c$ may be ascertained in block 306 or 320 (FIG. 4), as discussed above. Block 604 may involve evaluating the distances between the individual glints $Q_i$ and the image pupil center $p_c$. In the exemplary illustration of FIG. 18B, the closest glint $Q_i$ to the image pupil center $p_c$ is glint $Q_2$ and therefore block 604 would involve setting $Q_\alpha = Q_2$. In the illustrated embodiment, method 600 assumes that the closest glint $Q_\alpha$ to the image pupil center $p_c$ is a valid reference glint.

Method 600 then proceeds to block 606 which involves initializing a first reference point counter j by setting j=1 and initializing a global minimum distance $d_{min,global} = \infty$. As discussed in more detail below, the reference point counter j allows method 600 to iterate through the reference points $R_j$ (j=1 . . . N) and the global minimum distance $d_{min,global}$ is a parameter used in the method 600 pattern matching technique. Method 600 then proceeds to block 608, which involves an inquiry as to whether the first reference point counter j is greater than N. For the first iteration, the block 608 inquiry is negative and method 600 proceeds to block 610. Block 610 involves determining the translation $T_j$ required to move glint $Q_\alpha$ to the location of $R_j$. Since the first reference point counter j was just initialized to j=1 (block 606), the first iteration of block 610 involves determining the translation $T_1$ required to move glint $Q_\alpha$ to the location of $R_1$.

Figure 18C:
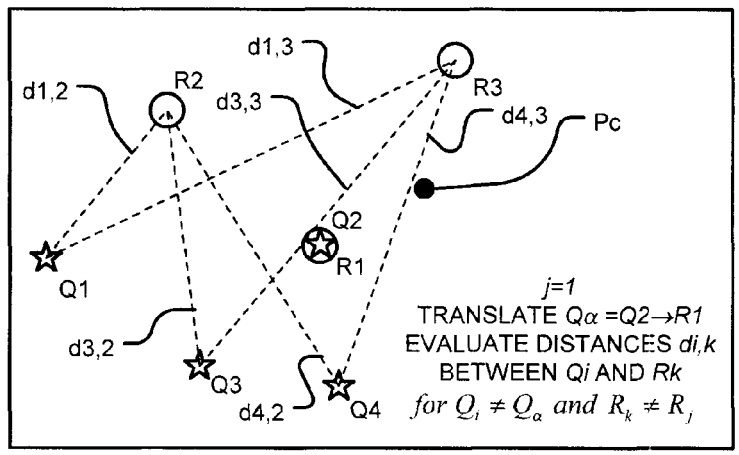

Method 600 then proceeds to block 612 which involves applying the block 610 translation $T_j$ to the detected glints $Q_i$ (i=1 . . . M). FIG. 18C shows the block 612 application of the block 610 translation $T_j$ for the exemplary embodiment for j=1 (i.e. the first iteration of blocks 610 and 612). Comparing FIGS. 18B and 18C, it may be seen that $Q_\alpha = Q_2$ is translated to the location of $R_j = R_1$ and that the other glints $Q_1$, $Q_3$, $Q_4$ have been translated by an equivalent translation $T_1$.

After applying the block 612 translation to the detected glints $Q_i$ method 600 involves cycling through the glints $Q_i$ (i=1 . . . M) and measuring the distance between each glint Qi and the reference points $R_j$ (j=1 . . . N) to detect distances which may be less than a threshold distance $d_{thresh}$. This process begins in block 614 which involves initializing a glint counter i. Block 614 may involve setting the glint counter to i=1. Although only one inquiry is expressly illustrated in FIG. 17B, block 616 may involve a pair of inquiries. A first inquiry involves inquiring as to whether i=α. If i=α, then block 616 may increment the glint counter i by one and return to block 616. It will be appreciated that there is no need to compute distances for the glint $Q_\alpha$, as the glint $Q_\alpha$ has been translated directly to a reference point $R_j$. The second block 616 inquiry involves an inquiry as to whether the glint counter i is greater than M. For the first iteration, the second block 616 inquiry is negative and method 600 proceeds to block 618.

Block 618 involves computing the distances $d_{i,k}$ between the current glint Qi and the reference points $R_k$ (k=1 . . . N, k≠j). The index k may be referred to herein as the second reference point counter. It will be appreciated that there is no need to compute distances for the reference point $R_k = R_j$, as the glint $Q_\alpha$ has been translated directly to a reference point $R_j$. The block 618 distance calculations $d_{i,k} = d_{1,2}$ and $d_{i,k} = d_{1,3}$ are illustrated in dashed lines in FIG. 18C for glint $Q_1$ of the exemplary configuration.

Method 600 then proceeds to block 620 which involves evaluating whether the minimum distance MIN($d_{i,k}$) determined in block 618 is the new global minimum distance $d_{min,global}$. In the first iteration of block 618, the global minimum distance $d_{min, global}$ is infinity (as initialized in block 606). As such, the minimum distance MIN($d_{i,k}$) determined in block 618 will be the new global minimum $d_{min, global}$ and the block 620 inquiry is positive (i.e. block 620 YES output). As such, method proceeds to block 622 which involves updating the global minimum $d_{min, global}$ by setting $d_{min, global}$ MIN($d_{i,k}$). Referring to FIG. 18C, it can be seen that the actual minimum distance MIN($d_{i,k}$) in the exemplary illustration $d_{i,k} = d_{1,2}$. Accordingly, in the FIG. 18C exemplary illustration, block 622 involves updating global minimum $d_{min, global}$ = MIN($d_{i,k}$) = $d_{1,2}$. Block 622 also involves assigning a mapping of $Q_\alpha \to R_j$. That is, a mapping is established between glint $Q_\alpha$ and reference point $R_j$. In the exemplary illustration of FIG. 18C, this block 622 mapping assignment involves assigning a mapping of $Q_\alpha = Q_2 \to R_j = R_1$.

Method 600 then proceeds to block 624 where the block 218 minimum distance MIN($d_{i,k}$) is compared to a threshold distance $d_{thresh}$. The threshold distance may be experimentally determined or otherwise calibrated such that when a block 218 distance $d_{i,k}$ is determined to be less than $d_{thresh}$, the glint $Q_i$ is highly likely to correspond to the reference point $R_k$. As such, if the block 218 minimum distance MIN($d_{i,k}$) is less than $d_{thresh}$ (block 624 YES output), then method 600 proceeds to block 628 which involves assigning a mapping of $Q_i \to R_k$ where the subscripts i, k refer to the same subscripts of the block 218 minimum distance MIN($d_{i,k}$). That is block 628 involves assigning a mapping of glint $Q_i$ to reference point $R_k$. In the illustrated example of FIG. 18C, the block 218 minimum distance MIN($d_{i,k}$)=$d_{1,2}$ is greater than $d_{thresh}$ (block 624 NO ouptut), so method 600 proceeds to block 626.

In block 626, the glint counter i is incremented by one (i.e. to i=2) before returning to block 616. As discussed above, block 616 involves an inquiry as to whether the glint counter i=α. Since i=α=2, block 616 will increment the glint counter i again, such that i=3. Blocks 618-626 are then repeated for the new glint $Q_i = Q_3$. Referring to FIG. 18C, it can be seen that for the illustrated example, the distances ($d_{i,k} = d_{3,2}$ and $d_{i,k} = d_{3,3}$) between glint $Q_3$ and reference points $R_2$ and $R_3$ are greater than both the global minimum $d_{min, global}$ and the threshold $d_{thresh}$. Consequently, no further mapping assignments are made in the i=3 iteration. The glint counter i is then incremented to i=4 and blocks 618-626 are repeated again for the new glint $Q_i = Q_4$. Referring to FIG. 18C, it can be seen that for the illustrated example, the distances ($d_{i,k} = d_{4,2}$ and $d_{i,k} = d_{4,3}$) between glint $Q_4$ and reference points $R_2$ and $R_3$ are greater than both the global minimum $d_{min, global}$ and the threshold $d_{thresh}$. Consequently, no further mapping assignments are made in the i=4 iteration.

When method returns to block 616 after the i=4 iteration, the block 616 inquiry is positive (i.e. block 616 YES output), so method 600 proceeds to block 630, where the first reference counter j is incremented by one before proceeding to the block 608 inquiry. In the illustrated example, block 630 involves setting the first reference counter j to j=2. In the illustrated example, since j=2≤N=3, the block 608 inquiry is negative (block 608 NO output). Method 600 then involves repeating blocks 610-630 for a second iteration where the glint $Q_\alpha$ (i.e. the glint closest to the image pupil center $p_c$) is translated to the second reference point $R_j = R_2$. The translated glints ($Q_1$, $Q_2$, $Q_3$, $Q_4$) and the glint-to-reference distances ($d_{1,1}$, $d_{1,3}$, $d_{3,1}$, $d_{3,3}$, $d_{4,1}$, $d_{4,3}$) for the second (j=2) iteration of the exemplary illustration are shown in FIG. 18C. As can be seen from FIG. 18C, for the illustrated example, the distance $d_{4,1}$ is a new global minimum $d_{min, global}$, so the block 620 inquiry will be positive for the i=4 iteration and block 622 will involve replacing the previous $Q_\alpha$ mapping with a mapping of $Q_\alpha = Q_2 \to R_j = R_2$. FIG. 18C also shows that none of the glint-to-reference distances ($d_{1,1}$, $d_{1,3}$, $d_{3,1}$, $d_{3,3}$, $d_{4,1}$, $d_{4,3}$) for the second (j=2) iteration are less threshold $d_{thresh}$. Consequently, method 600 does not make any block 628 assignments in the second (j=2) iteration.

Figure 18D:
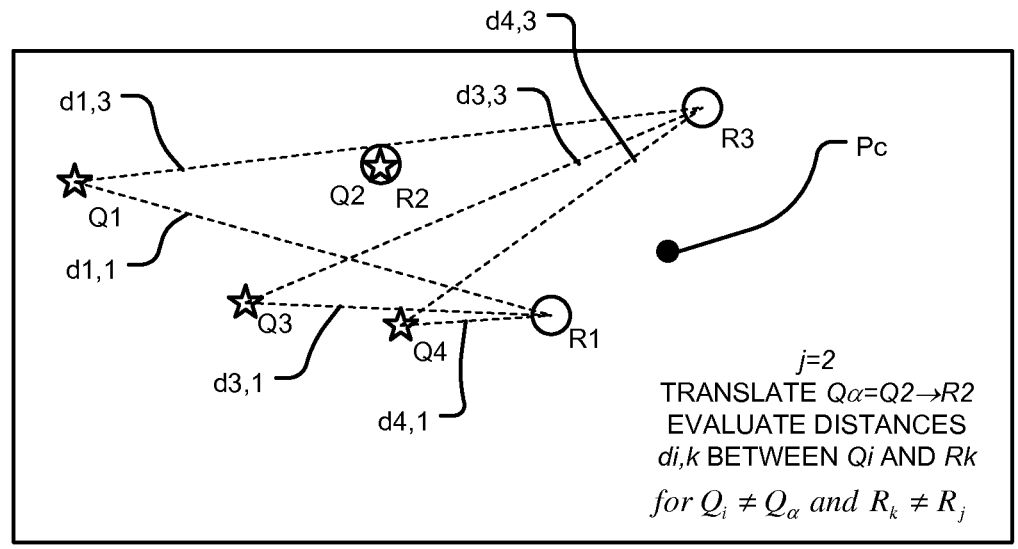
Figure 18E:
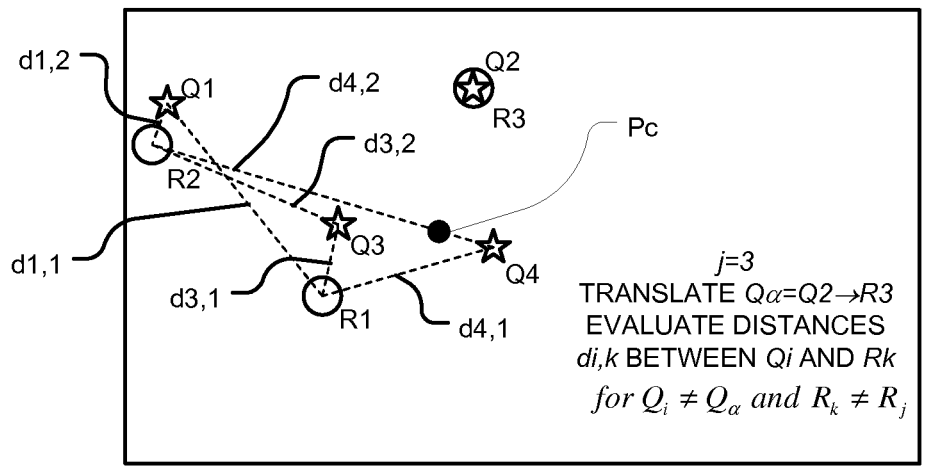

After evaluating the distances ($d_{1,1}$, $d_{1,3}$, $d_{3,1}$, $d_{3,3}$, $d_{4,1}$, $d_{4,3}$), method 600 returns to block 630, where the first reference counter j is incremented by one before proceeding to the block 608 inquiry. In the illustrated example, block 630 involves setting the first reference counter j to j=3. In the illustrated example, since j=3≤N=3, the block 608 inquiry is negative (block 608 NO output). Method 600 then involves repeating blocks 610-630 for a third iteration where the glint $Q_\alpha$ (i.e. the glint closest to the image pupil center $p_c$) is translated to the third reference point $R_j = R_3$. The translated glints ($Q_1$, $Q_2$, $Q_3$, $Q_4$) and the glint-to-reference distances ($d_{1,1}$, $d_{1,2}$, $d_{3,1}$, $d_{3,2}$, $d_{4,1}$, $d_{4,2}$) for the third (j=3) iteration of the exemplary illustration are shown in FIG. 18D. As can be seen from FIG. 18D, the translation involves in the third (j=3) iteration represents the best pattern matching between the glints $Q_i$ (i=1 . . . M) and the reference points $R_j$ (j=1 . . . N).

In the i=1 iteration of blocks 618-628, it can be seen from FIG. 18D that, in the illustrated example, the distance $d_{i,k} = d_{1,2}$ represents a new global minimum distance $d_{min,global}$, so the block 620 inquiry will be positive for the i=1 iteration and block 622 will involve replacing the previous $Q_\alpha$ mapping with a mapping of $Q_\alpha = Q_2 \rightarrow R_j = R_3$. Also, in the i=1 iteration, the block 624 inquiry is positive (i.e. the minimum distance MIN($d_{i,k}$)=$d_{1,2}$ is less than the threshold $d_{thresh}$), so method 600 enters block 628 where the glint $Q_i = Q_1$ is assigned to reference point $R_k = R_2$ corresponding to MIN($d_{i,k}$)=$d_{1,2}$. That is, block 628 involves making an assignment of $Q_i = Q_1 \rightarrow R_k = R_2$. Also, in the i=3 iteration, the block 624 inquiry is once again positive for the minimum distance MIN($d_{i,k}$)=$d_{3,1}$ (i.e. the minimum distance MIN($d_{i,k}$)=$d_{3,1}$ is less than the threshold $d_{thresh}$), so method 600 enters block 628 where the glint $Q_i = Q_3$ is assigned to reference point $R_k = R_1$ corresponding to MIN($d_{i,k}$)=$d_{3,1}$. That is, block 628 involves making an assignment of $Q_i = Q_3 \rightarrow R_k = R_1$.

Accordingly, in the illustrated example, at the conclusion of the third (j=3) iteration, method 600 has made the following mapping assignments:

$Q_2 \rightarrow R_3$—assigned in block 622 during the i=1 iteration;
$Q_1 \rightarrow R_2$—assigned in block 628 during the i=1 iteration; and
$Q_3 \rightarrow R_1$—assigned in block 628 during the i=3 iteration.

Since the mapping between the reference points $R_j$ and the off-axis lights 224A is known from block 602, these mapping assignments are equivalent to mappings between the detected off-axis glints $Q_1, Q_2, Q_3$ and the off-axis lights 224A. When method 600 returns to block 630, the first reference counter j is again incremented. In the illustrated example, the first reference counter j is incremented to j=4. Thus, when method 600 returns to block 608, the block 608 inquiry is positive (i.e. N=3 in the illustrated example). As such, method 600 ends in block 632.

Method 600 shown in FIGS. 17A and 17B compensates for translation, distortion, addition and deletion of block 322 glints. For this reason, it may be desirable to set the block 322 glint-detection threshold (actually implemented in block 378 of method 370 (FIG. 7)) to a relatively low value, so as to accept false positive glints, which will ultimately be rejected during method 600 pattern matching. Using pattern matching method 600, the presence of false positive glints may produce a better result than rejecting a glint because it did not meet the block 378 glint-detection threshold. Since the block 322 glints are reflections from an at least quasi-spherical surface (the cornea), rotation of the image pattern should not be present. In addition, by tuning the threshold value $d_{thresh}$, method 600 may accommodate changes in scale due to the depth of the user's eyes. The depth of the user's eyes may change with head movement, for example. In some embodiments, off-axis lights 224A may be positioned at irregular (i.e. non-symmetrical) locations to avoid the possibility that pattern matching method 600 could map multiple patterns of imaged glints Qi to the pattern of reference points $R_j$.

After mapping the block 322 off-axis glints $Q_i$ to off-axis lights 224A in block 323 (FIG. 4), method 300 proceeds to block 324 which involves an inquiry into whether or not the user is wearing glasses. The block 324 inquiry may involve a procedure similar to the block 308 inquiry. In some embodiments, the block 324 inquiry may use the answer obtained from the block 308 inquiry or may depend on user input. If no eyeglasses are detected (block 324 NO output), then method 300 proceeds to block 330 where it loops back to block 302. On the other hand, if eyeglasses are detected (block 324 YES output), then method 300 proceeds to block 326. Block 326 involves an inquiry as to whether method 300 can accurately extract two or more glints from the dark pupil image in block 322 and match these two or more glints to corresponding off-axis lights 224A in block 323. If two or more pupil glints are detectable without issues in block 322 and matchable to off-axis lights 224A in block 323 (block 326 YES output), then method 300 proceeds to block 330 where it loops back to block 302. On the other hand, if method 300 fails to obtain a pair of pupil glints in block 322 (block 326 NO output), then the off-axis lights 224A used for the LOS determination may be changed in block 328 before proceeding to block 330 and looping back to block 302. In some embodiments, the block 326 inquiry may be modified such that a number of failed glint-detection or glint-matching iterations are required before a NO output is decided and the off-axis lights 224A are changed in block 328.

Figure 9:
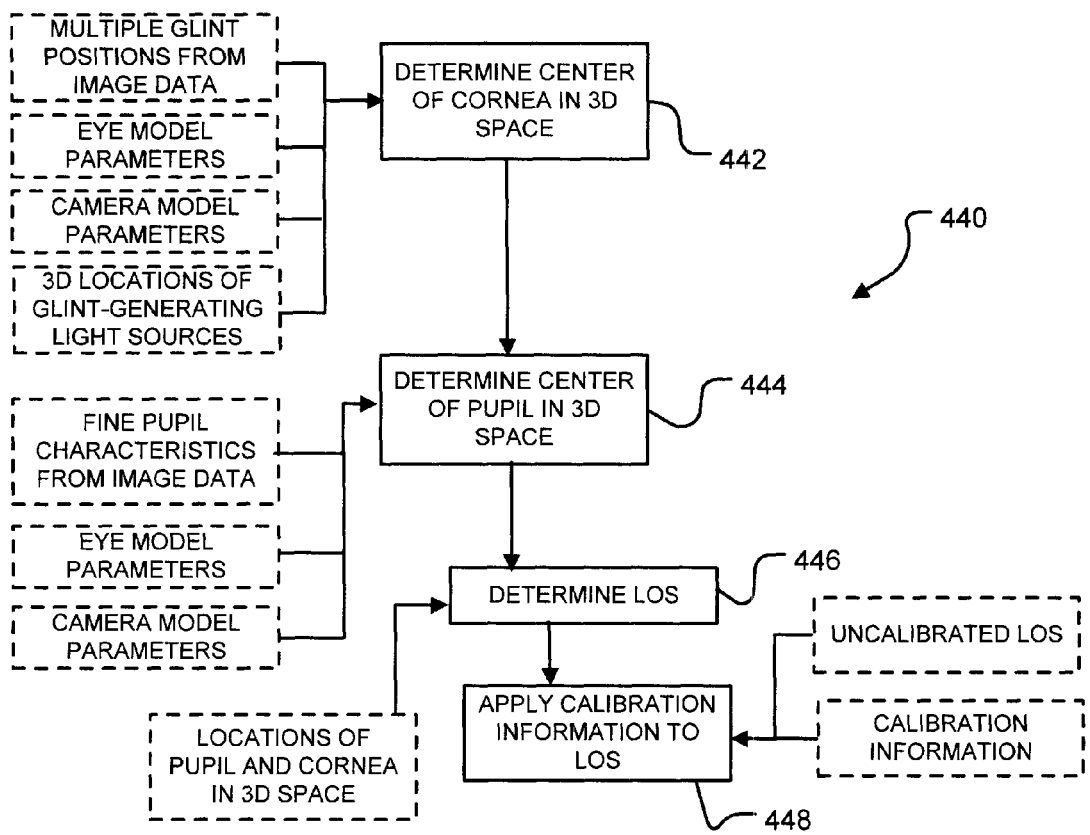
FIG. 9 schematically depicts a particular embodiment of a method for using the multiple glint and fine pupil information obtained in the method of FIG. 4 to estimate the LOS vector for one of the user's eyes.

As explained briefly above, the data extracted from method 300 are used to determine the LOS for each of the user's eyes. In one particular embodiment a model-based approach is used to determine the LOS. FIG. 9 is a schematic illustration of a method 440 for using the pupil and glint data determined in method 300 to estimate the LOS vector for a particular eye. It will be appreciated that method 440 may be performed for each of the user's eyes to determine the LOS vector for each eye. Some of the operational details of processes similar to the functional operation of the method 440 processes are described for determining the 2-dimensional point-of-gaze (POG) for one eye in Hennessey, which, as discussed above, is incorporated herein by reference.

Figure 10:
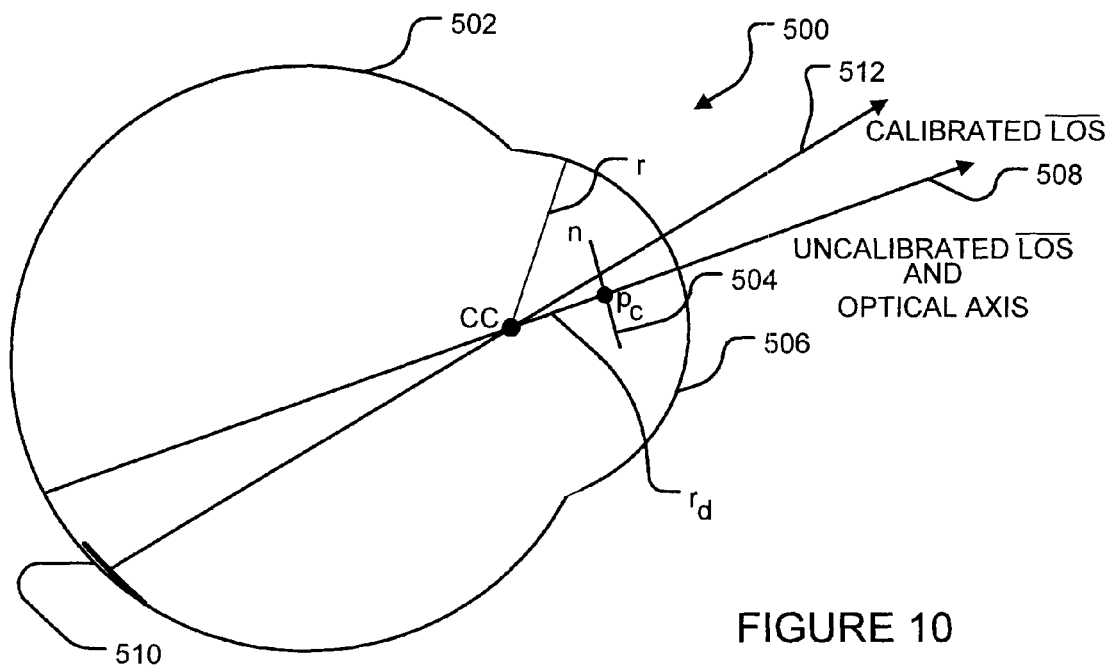
FIG. 10 is a schematic illustration of the geometry involved in the FIG. 9 method of using the multiple glint and fine pupil information to determine the LOS vector.

Method 440 involves using a model of the user's eye. The eye model is represented in a principal coordinate system which also includes the scene that is presented to the user. An eye model 500 suitable for use in method 440 is schematically illustrated in FIG. 10. In model 500, eye 502 includes pupil 504, cornea 506 and fovea 510. In the illustrated model 500, cornea 506 is assumed to be spherical with a center CC and a radius r. In model 500, $P_c$ represents the center of pupil 504 in the principal coordinate system and the parameter $r_d$ represents the distance between model pupil center $P_c$ and CC (i.e. the distance between the centers of cornea 506 and pupil 504). The geometrical parameters CC, r, $P_c$ and $r_d$ of eye model 500 are represented in a principal coordinate system. Model 500 also incorporates a parameter n, which represents the index of refraction of the aqueous humor fluid.

In particular embodiments, the parameters n, r and $r_d$ may be based on population averages determined experimentally or otherwise. In other embodiments, these parameters may be measured or otherwise determined or calibrated on a per-user basis. The purpose of method 440 (FIG. 9) is to determine the LOS vector ($\overline{LOS}$) for one of the user's eyes in the principal coordinate system. In accordance with model 500 of the illustrated embodiment, the uncalibrated LOS vector 508 is the line that extends from the center CC of cornea 506 through the model pupil center $P_c$ of pupil 504. The line that extends from the center CC of cornea 506 through the model pupil center $P_c$ of pupil 504 is also referred to as the "optical axis" 508 of eye model 500. Uncalibrated LOS vector 508 may then be calibrated to arrive at calibrated LOS vector 512. As explained in more detail below, calibration may help to correct for the offset of fovea 510 from optical axis 508.

Method 440 begins in block 442 which involves using data from a plurality of glints to determine the parameter CC (i.e. the three-dimensional location of the center of cornea 506 in the principal coordinate system). In particular embodiments, the block 442 determination comprises a geometrical calculation which makes use of: image information obtained in block 322 (FIG. 4) for at least a pair of off-axis glints from the dark pupil image; parameters of eye model 500 (e.g. r); a camera model; known three-dimensional locations of off-axis lights 224A; and the block 323 mapping between the block 322 off-axis glints and the off-axis lights 224A. In particular embodiments, the off-axis glints used for the block 442 determination of the cornea center CC are selected to be the two glints which are closest to the image pupil center $p_c$ provided that the block 323 mapping information is known for these glints—see the exemplary illustration of FIG. 18B. These two glints closest to the image pupil center $p_c$ may be referred to as the "selected" glints. In particular embodiments, the camera model used in block 442 is a standard pinhole camera model which includes camera parameters of effective focal length f and critical point cp (i.e. the center of the image plane). This pinhole camera model is explained in Hennessey.

In one particular embodiment, the block 442 geometrical calculation involves a triangulation procedure. In this triangulation procedure, for each of the selected glints, the following parameters are transformed from the principal coordinate system to a secondary coordinate system: the image location of the selected glint (as determined in block 322), the corresponding glint location on the surface of cornea 506, the location of cornea center CC in model 500 and the location of the corresponding off-axis light source 224A which maps to the selected glint. For each of the selected glints, the secondary coordinate system is chosen such that these parameters are located on a single axial plane. Equations representing the location of the cornea center CC in each of these secondary coordinate systems may be determined geometrically. However, when transformed back to the principal coordinate system, the cornea center CC generated in each secondary coordinate system must be the same. This constraint results in a over-defined set of non-linear equations expressed in terms of the unknown locations of the selected glints on corneal surface 506 in their corresponding secondary coordinate systems. This system of equations may be solved numerically using a number of computational techniques known to those skilled in the art. One non-limiting example of a technique for solving over-defined systems of non-linear equations is Newton's method (also known as the Newton-Raphson method). The cornea center CC can then be calculated on the basis of either of the estimated values for the locations of the selected glints on the corneal surface in their corresponding secondary coordinate systems. A particular technique for implementing the block 442 geometrical calculation is described in Hennessey. While particular embodiments make use of a pair of selected glints, it will be appreciated that three or more glints may be "selected" for use in the block 442 procedure to determine the cornea center CC.

After determining the location of the cornea center CC in block 442, method 440 proceeds to block 444 which involves determining the location of the model pupil center $P_c$ in the principal coordinate system. In one particular embodiment, the block 444 pupil center determination makes use of the fine pupil characteristics obtained in block 320, the camera model information and the parameters of eye model 500 (e.g. r, $r_d$, n) to trace a ray from the center of pupil in the image data (i.e. the image pupil center $p_c$) to the model pupil center $P_c$ of the pupil 504 in eye model 500. In such a ray tracing, it is assumed that the model pupil center $P_c$ of model 500 is imaged to the pupil image center $p_c$ of the block 320 fine pupil characteristics. When performing this ray tracing, it is necessary to take into account the refraction of the ray at the surface of cornea 506 due to the index of refraction n in the aqueous humor fluid.

In some embodiments, it is desirable to trace rays from multiple points in the block 320 fine pupil image data as a part of block 444 to improve the accuracy of the determination of model pupil center $P_c$. For example, block 444 may involve tracing rays from a plurality of points on a perimeter of the block 320 fine pupil in the image data into eye model 500 to determine perimeter points on pupil 504 of eye model 500. Block 444 may involve tracing one or more opposing pairs of perimeter fine pupil image points onto pupil 504 of eye model 500 in the principal coordinate system and then calculating an average of the pupil perimeter points in the principal coordinate system to be the model pupil center $P_c$. Opposing pairs or of perimeter fine pupil image points may be selected as being angularly equidistant from the major and/or minor axes of the ellipse fit to the fine pupil data in block 422. In some embodiments, groups of other sizes (i.e. other than pairs) of perimeter pupil image points may be selected from locations equally angularly spaced around the fine pupil ellipse. The number of perimeter pupil image points which may be traced may depend on processing resources. It will be appreciated that using a larger number of perimeter pupil image points will result in a more accurate result (e.g. less susceptibility to noise), but is more computationally expensive. In some embodiments, the number of perimeter pupil image points used in block 444 is in a range of 2-20. A particular technique for implementing the block 444 ray tracing is described in Hennessey.

After determining the model pupil center $P_c$ in block 444, method 440 proceeds to block 446 which involves determining the uncalibrated LOS vector ($\overline{LOS}$) 508 for the particular eye in the principal coordinate system. In particular implementations, the block 446 determination of uncalibrated $\overline{LOS}$ 508 makes use of the cornea center CC (from block 442) and the model pupil center $P_c$ (from block 444). In one particular embodiment, the block 446 determination of uncalibrated $\overline{LOS}$ 508 involves tracing a ray from the cornea center CC through the model pupil center $P_c$. The block 446 uncalibrated $\overline{LOS}$ 508 represents the LOS vector for one of the user's eyes and may used in block 120 or block 130 of method 100 (FIG. 1) to determine the user's three-dimensional POG, as discussed in detail above.

Improved results may be obtained by applying calibration information to the block 446 uncalibrated $\overline{LOS}$ 508 to obtain a calibrated $\overline{LOS}$ 512 in block 448 and using calibrated Los 512 in block 120 or block 130 of method 100 (FIG. 1) to determine the user's three-dimensional POG. The application of calibration information in block 448 is an optional procedure. By way of non-limiting example, such calibration adjustment may be used to account for inaccuracies in: measurement of the physical locations of the off-axis lights 224A used to generate glints in the dark pupil image; the camera model parameters; and the variations in the eyes of individual users from eye model 500 used in method 440 and the offset of fovea 510 from optical axis 508 of eye model 500. Before applying calibration information in block 448, such calibration information must be obtained.

Figures 11, 12:
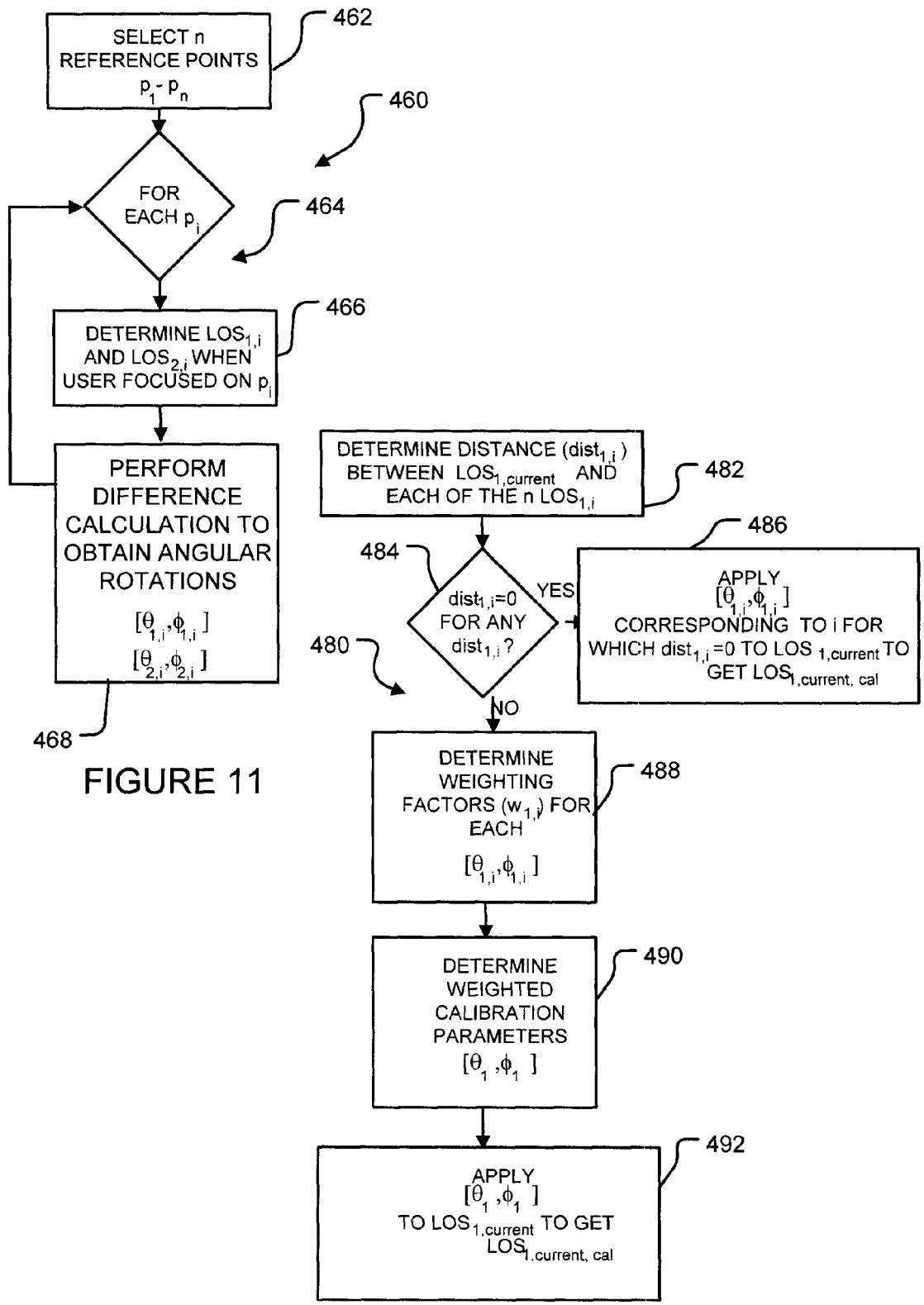
FIG. 11 schematically illustrates a method for obtaining calibration values which may be used to calibrate or otherwise adjust the POG estimate obtained using the method of FIG. 1.
FIG. 12 schematically illustrates a method for applying weights to the calibration values determined in FIG. 11 and for adjusting the POG estimate obtained using the method of FIG. 1 using the weighted calibration values.

FIG. 11 illustrates a method 460 for obtaining calibration information according to a particular embodiment of the invention. Method 460 begins in block 462 which involves selecting a plurality of known reference points $p_i$ in the three-dimensional space of the scene presented to the user. Preferably, the reference points $p_i$ selected in block 462 are spaced apart over the scene (i.e. the region in which it is desired to track the user's three-dimensional POG). The number n of reference points $p_i$ in block 462 may be selected to balance the desire for optimum calibration with the desire to reduce the calibration time required.

Figure 14:
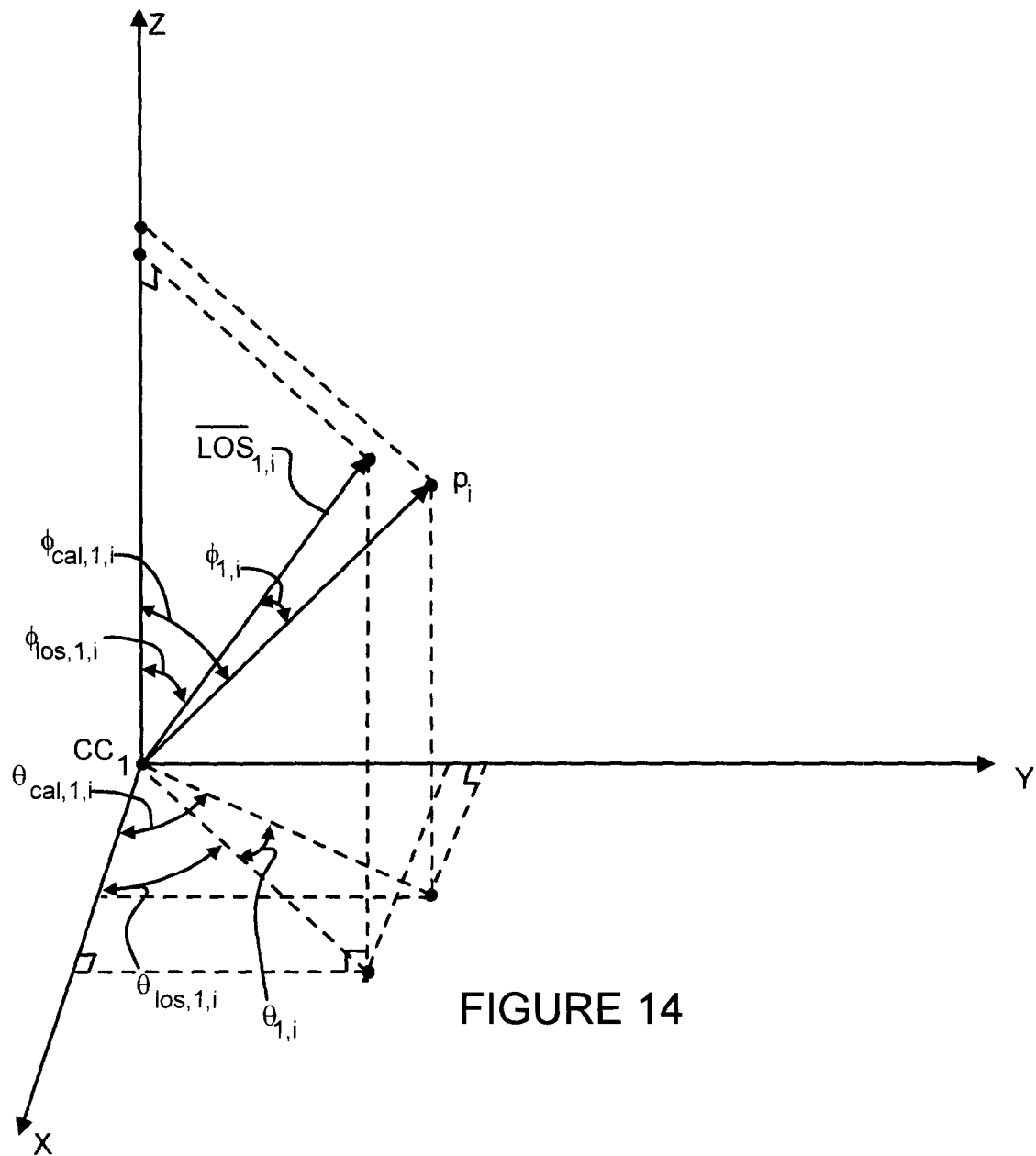
FIG. 14 schematically illustrates the determination of an $i^{th}$ calibration parameters for the first eye.

Method 460 then performs a calibration loop 464 for each of the n reference points $p_i$. In each iteration of calibration loop 464, a user is asked to focus on one of the reference points $p_i$. In block 466, the above described methods are used to estimate the uncalibrated $\overline{LOS}$ 508 for each of the user's eyes when the user is focused on the reference point $p_i$. The uncalibrated $\overline{LOS}$ 508 for the user's eyes when the user is focused on the $i^{th}$ reference point $p_i$ may be designated as $\overline{LOS}_{1,j}, \overline{LOS}_{2,i}$ where $\overline{LOS}_{1,i}$ represents the block 446 uncalibrated $\overline{LOS}$ 508 of the first eye when it is focused on the $i^{th}$ reference point $p_i$ and $\overline{LOS}_{2,i}$ represents the block 446 uncalibrated $\overline{LOS}$ 508 of the second eye when it is focused on the $i^{th}$ reference point $p_i$. The term $\overline{LOS}_{1,j}$ may be referred to as the "$i^{th}$ calibration LOS value for the first eye" and the term $\overline{LOS}_{2,i}$ may be referred to as the "$i^{th}$ calibration value for the second eye". FIG. 14 schematically depicts the $i^{th}$ reference point $p_i$ and the $i^{th}$ calibration LOS value for the first eye ($\overline{LOS}_{1,i}$). It is assumed, for simplification, that the corneal center $CC_1$ of the first eye (shown as the origin in FIG. 14) coincides with the center of rotation of the first eye. While the actual center of rotation of the first eye is unknown, it is assumed that the center of rotation is at least relatively close to the corneal center $CC_1$.

In general, the $i^{th}$ calibration LOS values ($\overline{LOS}_{1,i}, \overline{LOS}_{2,i}$) may not intersect exactly with reference point $p_i$. This is shown in FIG. 14 for $\overline{LOS}_{1,i}$. It can be seen from FIG. 14 that $\overline{LOS}_{1,i}$ may be characterized, at least in part, by the angles $[\theta_{los,1,i}, \phi_{los,1,i}]$ and that a vector from the corneal center $CC_1$ of the first eye intersecting point $p_i$ may be characterized, at least in part, by the angles $[\theta_{cal,1,i}, \phi_{cal,1,i}]$. Block 468 (FIG. 11) involves determining a set of angular rotations $[\theta_{1,i}, \phi_{1,i}]$ which, when added to $[\theta_{los,1,i}, \phi_{los,1,i}]$ to rotate $\overline{LOS}_{1,i}$ about cornea center $CC_1$, will shift $\overline{LOS}_{1,i}$ to intersect reference point $p_i$ and a set of angular rotations $[\theta_{2,i}, \phi_{2,i}]$ which, when added to $[\theta_{los,1,i}, \phi_{los,1,i}]$ to rotate $\overline{LOS}_{2,i}$ about cornea center $CC_2$, will shift $\overline{LOS}_{2,i}$ to intersect reference point $p_i$. That is, block 468 involves determining $[\theta_{1,i}, \phi_{1,i}]$ and $[\theta_{2,i}, \phi_{2,i}]$ which satisfy:

$$\begin{bmatrix} \theta_{cal,1,i} \\ \phi_{cal,1,i} \end{bmatrix} = \begin{bmatrix} \theta_{los,1,i} + \theta_{1,i} \\ \phi_{los,1,i} + \phi_{1,i} \end{bmatrix} \quad (5)$$

and $$\begin{bmatrix} \theta_{cal,2,i} \\ \phi_{cal,2,i} \end{bmatrix} = \begin{bmatrix} \theta_{los,2,i} + \theta_{2,i} \\ \phi_{los,2,i} + \phi_{2,i} \end{bmatrix} \quad (6)$$

The angular rotations $[\theta_{1,i}, \phi_{1,i}]$ determined in block 468 may be referred to as the "$i^{th}$ set of calibration parameters for the first eye" and the angular rotations $[\theta_{2,i}, \phi_{2,i}]$ determined in block 468 may be referred to as the "$i^{th}$ set of calibration parameters for the second eye".

In one particular embodiment, the block 468 determination of the $i^{th}$ set of calibration parameters for the first and second eyes ($[\theta_{1,i}, \phi_{1,i}], [\theta_{2,i}, \phi_{2,i}]$) proceeds as follows. It can easily be shown from the geometry of FIG. 14, that:

$$\begin{bmatrix} \overline{LOS_{1,i}} \\ \|\overline{LOS_{1,i}}\| \end{bmatrix} = \begin{bmatrix} LOS_{1,i,x} \\ LOS_{1,i,y} \\ LOS_{1,i,z} \end{bmatrix} = \begin{bmatrix} \sin\phi_{los,1,i}\cos\theta_{los,1,i} \\ \sin\phi_{los,1,i}\sin\theta_{los,1,i} \\ \cos\phi_{los,1,i} \end{bmatrix} \quad (7)$$

Based on equation (7), the $i^{th}$ calibration LOS value for the first eye ($\overline{LOS}_{1,i}$) may be used to solve for $[\theta_{los,1,i}, \phi_{los,1,i}]$. Similarly, $i^{th}$ calibration LOS value for the second eye ($\overline{LOS}_{2,i}$) may be used to solve for $[\theta_{los,2,i}, \phi_{los,2,i}]$. The parameters $[\theta_{cal,1,i}, \phi_{cal,1,i}]$ and $[\theta_{cal,2,i}, \phi_{cal,2,i}]$ may be determined using a similar geometric calculation based on the known coordinates of the $i^{th}$ reference point $p_i$. Then, equations (5) and (6) may be solved to resolve the $i^{th}$ set of calibration parameters for the first eye ($[\theta_{1,i}, \phi_{1,i}]$) and the $i^{th}$ set of calibration parameters for the second eye ($[\theta_{2,i}, \phi_{2,i}]$).

Referring back to FIG. 11, after looping through each of the n reference points $p_i$, method 460 concludes when it has determined n sets of calibration parameters for the first eye $[\theta_{1,i}, \phi_{1,k}]|_{i=1,2\ldots n}$ and n sets of calibration parameters for the second eye $[\theta_{2,i}, \phi_{2,i}]|_{1,2\ldots n}$.

Figure 15:
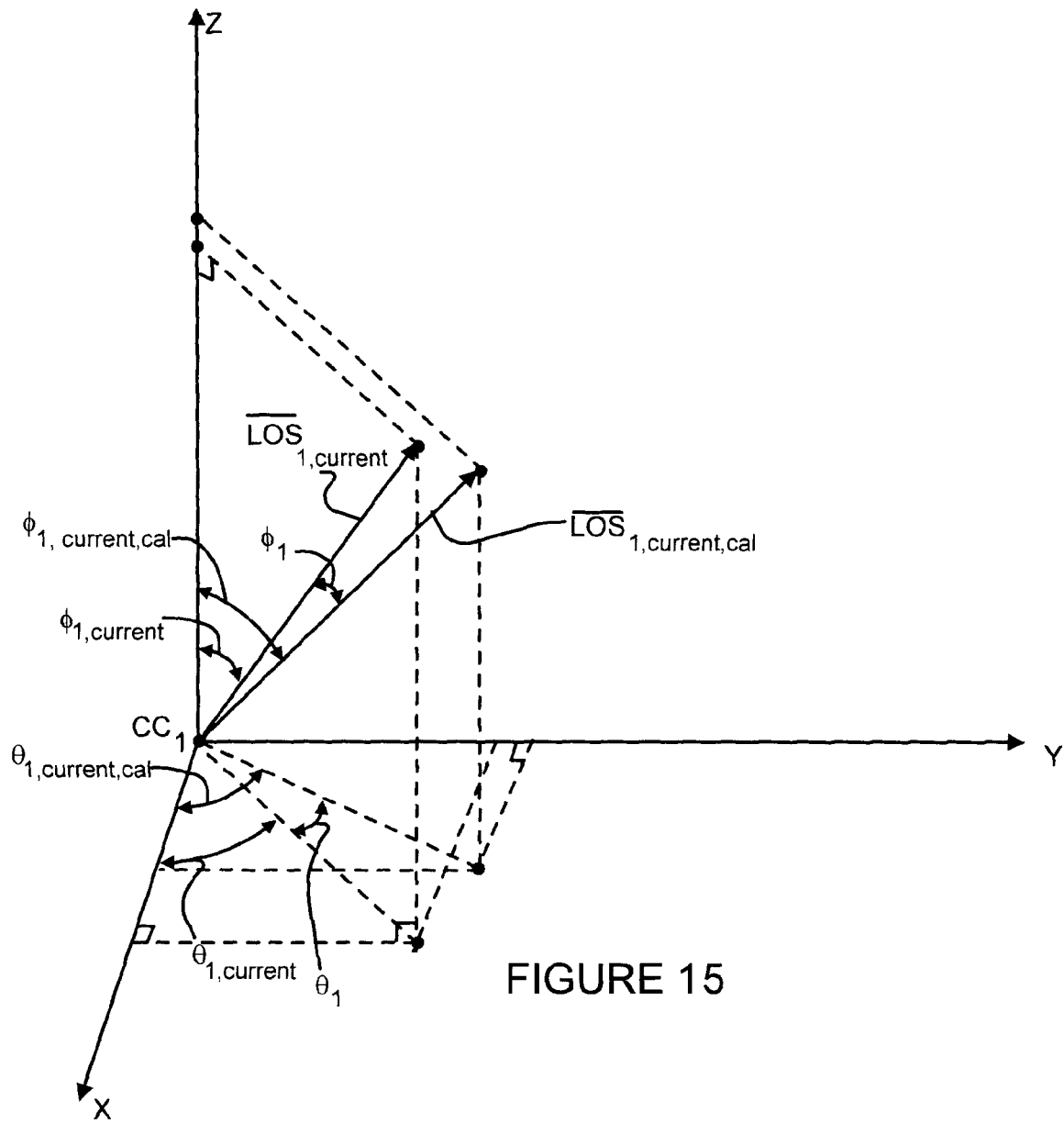
FIG. 15 schematically illustrates the application of weighted calibration parameters to the uncalibrated LOS vector for the first eye.

FIG. 12 schematically depicts a method 480 for applying calibration information to the block 446 (FIG. 9) uncalibrated LOS vector 508. The method 480 application of calibration information to uncalibrated LOS vector 508 may be implemented in block 448 (see FIG. 9). Method 480 of FIG. 12 may be implemented independently on each of the user's eyes. Method 480 is shown and described in relation to the user's first eye, but it will be appreciated that the application of calibration information to the block 446 uncalibrated LOS vector 508 for the other one of the user's eyes may be substantially similar. For the purposes of explaining method 480, the current block 446 uncalibrated LOS vector 508 for the first eye is referred to as $\overline{LOS}_{1,current}$ and the current block 448 calibrated LOS vector 512 for the first eye is referred to as $\overline{LOS}_{1,current,cal}$. An example showing the current block 446 uncalibrated LOS vector 508 for the first eye ($\overline{LOS}_{1,current}$) and the current block 448 calibrated LOS vector 512 for the first eye ($\overline{LOS}_{1,current,cal}$) is schematically illustrated in FIG. 15.

Method 480 commences in block 482 where a distance ($dist_{1,i}$) is determined between the current uncalibrated LOS vector $\overline{LOS}_{1,current}$ for the first eye and each of the n block 466 calibration LOS values $\overline{LOS}_{1,i}$ for the first eye. For the calibration LOS value $\overline{LOS}_{1,i}$, the distance $dist_{1,i}$ may be determined according to:

$$dist_{1,i} = \|LOS_{1,current} - \overline{LOS}_{1,i}\| \quad (8)$$

where $\|\bullet\|$ represents the norm operator. The output of block 482 includes n distinct $dist_{1,i}$ values corresponding to each of the n calibration LOS values $\overline{LOS}_{1,i}$ for the first eye. In other embodiments, other metrics (i.e. other than the geometrical norm) may be used to determine the $dist_{1,i}$ values.

Method 480 then proceeds to block 484 which involves an inquiry into whether any of the $dist_{1,i}$ values are zero. If the block 484 inquiry is negative (i.e. none of the $dist_{1,i}$ values are zero—block 484 NO output), then method 480 proceeds to block 488. Block 488 involves determining n weighting factors $w_{1,i}$ (i.e. one weighting factor corresponding to each of the n sets of calibration parameters $[\theta_{1,i}, \phi_{1,i}]$). According to one particular embodiment, the $i^{th}$ weighting factor $w_{1,i}$ for the first eye may be calculated in block 488 according to:

$$w_{1,i} = \frac{1}{dist_{1,i} \cdot \sum_{i=1}^{n} \frac{1}{dist_{1,i}}} \quad (9)$$

Where $w_{1,i}$ is a weighting factor proportional to the inverse of $dist_{1,i}$—i.e. the smaller $dist_{1,i}$ becomes, the closer $w_{1,i}$ gets to unity.

Method 480 then proceeds to block 490 which involves calculating the weighted calibration parameters $[\theta_1, \phi_1]$ to be applied to the current uncalibrated LOS vector $\overline{LOS}_{1,current}$ for the first eye. In one particular embodiment, the weighted calibration parameters $[\theta_1, \phi_1]$ may be calculated in block 490 according to:

$$\theta_1 = \sum_{i=1}^{n} w_{1,i} \theta_{1,i} \quad (10)$$

and $$\phi_1 = \sum_{i=1}^{n} w_{1,i} \phi_{1,i} \quad (11)$$

Method 480 then proceeds to block 492, where the weighted calibration parameters $[\theta_1, \phi_1]$ are applied to the current uncalibrated LOS vector $\overline{LOS}_{1,current}$ to obtain the calibrated LOS vector $\overline{LOS}_{1,current,cal}$. The block 492 application of the weighted calibration parameters $[\theta_1, \phi_1]$ to $\overline{LOS}_{1,current}$ may involve rotating $\overline{LOS}_{1,current}$ by the angles $[\theta_1, \phi_1]$ about the corneal center $CC_1$ of model 500 for the first eye to obtain $\overline{LOS}_{1,current,cal}$. A particular embodiment of the block 492 application of the weighted calibration parameters $[\theta_1, \phi_1]$ to $\overline{LOS}_{1,current}$ is schematically illustrated in FIG. 15. It can easily be shown from the geometry of FIG. 15, that:

$$\left[ \frac{\overline{LOS}_{1,current}}{\|\overline{LOS}_{1,current}\|} \right] = \begin{bmatrix} LOS_{1,current,x} \\ LOS_{1,current,y} \\ LOS_{1,current,z} \end{bmatrix} = \begin{bmatrix} \sin\phi_{1,current}\cos\theta_{1,current} \\ \sin\phi_{1,current}\sin\theta_{1,current} \\ \cos\phi_{1,current} \end{bmatrix} \quad (12)$$

Based on equation (12), the current uncalibrated LOS vector $\overline{LOS}_{1,current}$ may be used to solve for $[\theta_{1,current}, \phi_{1,current}]$. The weighted calibration parameters $[\theta_1, \phi_1]$ may then be added to angles $[\theta_{1,current}, \phi_{1,current}]$ associated with the current uncalibrated LOS vector $\overline{LOS}_{1,current}$ to obtain corresponding angles $[\theta_{1,current,cal}, \phi_{1,current,cal}]$ associated with the calibrated LOS vector $\overline{LOS}_{1,current,cal}$ in accordance with:

$$\begin{bmatrix} \theta_{1,current,cal} \\ \phi_{1,current,cal} \end{bmatrix} = \begin{bmatrix} \theta_{1,current} + \theta_1 \\ \phi_{1,current} + \phi_1 \end{bmatrix} \quad (13)$$

and the calibrated LOS vector $\overline{LOS}_{1,current,cal}$ may then be calculated using $[\theta_{1,current,cal}, \phi_{1,current,cal}]$ in accordance with:

$$\left[ \frac{\overline{LOS}_{1,current,cal}}{\|\overline{LOS}_{1,current,cal}\|} \right] = \begin{bmatrix} LOS_{1,current,cal,x} \\ LOS_{1,current,cal,y} \\ LOS_{1,current,cal,z} \end{bmatrix} \quad (14)$$

$$= \begin{bmatrix} \sin\phi_{1,current,cal}\cos\theta_{1,current,cal} \\ \sin\phi_{1,current,cal}\sin\theta_{1,current,cal} \\ \cos\phi_{1,current,cal} \end{bmatrix}$$

In summary, the method 480 calibration process adds a set of weighted calibration parameters $[\theta_1, \phi_1]$ to the angles $[\theta_{los,1,i}, \phi_{los,1,i}]$ associated with the current uncalibrated LOS vector $\overline{LOS}_{1,current}$ to obtain the angles $[\theta_{1,current,cal}, \phi_{1,current,cal}]$ associated with the calibrated LOS vector $\overline{LOS}_{1,current,cal}$. The weighted calibration parameters $[\theta_1, \phi_1]$ are a linear combination of n individual sets of calibration parameters $[\theta_{1,i}, \phi_{1,i}]|_{i=1\ldots n}$ and the weight w 1, applied to the $i^{th}$ individual set of calibration parameters $[\theta_{1,i}, \phi_{1,i}]$ depends on the proximity of the current uncalibrated LOS vector $\overline{LOS}_{1,current}$ to the $i^{th}$ calibration LOS value $\overline{LOS}_{1,i}$.

If one of the $dist_{1,i}$ values is zero (block 484 YES output), then the current uncalibrated LOS vector $\overline{LOS}_{1,current}$ is the same as the corresponding one of the n calibration LOS values $\overline{LOS}_{1,i}$ and method 480 proceeds to block 486. Block 486 may involve adding the unweighted calibration parameters $[\theta_{1,i}, \phi_{1,i}]$ corresponding to the value of i for which $dist_{1,i}=0$ directly to the angles $[\theta_{los,1,i}, \phi_{los,1,i}]$ associated with the current uncalibrated LOS vector $\overline{LOS}_{1,current}$ to obtain the angles $[\theta_{1,current,cal}, \phi_{1,current,cal}]$ associated with the calibrated LOS vector $\overline{LOS}_{1,current,cal}$. This may be accomplished using a process similar to the process of block 492 described above, except that the weighted calibration parameters $[\theta_1, \phi_1]$ are replaced with the unweighted calibration parameters $[\theta_{1,i}, \phi_{1,i}]$ corresponding to the value of i for which $dist_{1,i}=0$.

Another technique that may be used in particular embodiments to improve the method 100 POG estimation involves the use of one or more finite impulse response (FIR) moving average filters which may remove some of the high frequency jitter experienced in the method 100 POG estimation technique. The filtering procedures described below may be performed in addition to the calibration procedures described above. In some embodiments, FIR filtering may be performed by a suitably programmed digital signal processing (DSP) unit which may be a part of, or otherwise controlled by, controller 220. The general operation of FIR moving average filters are well known to those skilled in the art.

In some embodiments, FIR moving average filters may be applied to various elements of method 100 (FIG. 1). In one particular embodiment, the three-dimensional POG determined in block 140 may be filtered using a FIR moving average filter. In addition or in the alternative, other parameters which may be filtered include, without limitation: the directions of the calibrated or uncalibrated LOS vectors (block 446, block 448, block 120, and/or block 130); fine pupil information (block 320); the locations of the multiple glints (block 322); the locations of cornea centers $CC_1$, $CC_2$ (block 442); and/or the locations of model pupil centers $P_{c1}$, $P_{c2}$ (block 444). It will be appreciated that some of these filters may be applied independently to the parameter(s) of both of the user's eyes. These moving average filters may be applied on each iteration of method 100 (FIG. 1), method 300 (FIG. 4), method 350 (FIG. 6), method 370 (FIG. 7), method 400 (FIG. 8), method 600 (FIGS. 17A, 17B), method 440 (FIG. 9), method 480 (FIG. 12) and/or any of the other methods described herein.

Figure 13:
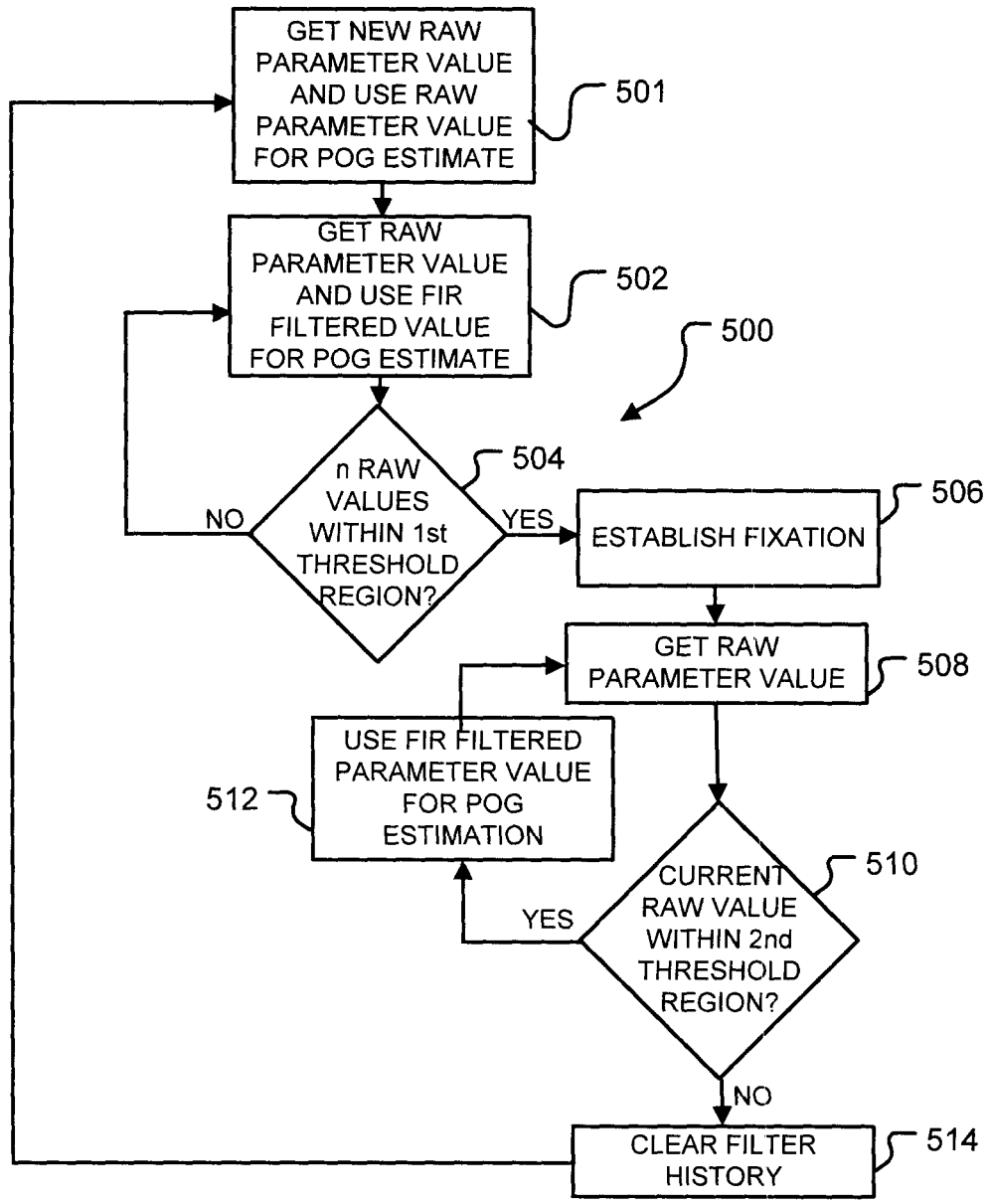
FIG. 13 schematically depicts a method for applying moving average filters to various parameters of the FIG. 1 method.

In some embodiments, the filtering process includes a method for fixation detection which detects when one or more parameters associated with the user's POG has shifted significantly and, in response to such a shift, clears the filter history to avoid spurious results which may otherwise be caused by the moving average filter. By way of non-limiting example, parameters for which detection of a significant shift may cause a filter clearing event include: the three-dimensional POG estimate itself, the directions of the calibrated or uncalibrated LOS vectors, fine pupil information in the image data; the locations of the multiple glints in the image data; the locations of cornea centers $CC_1$, $CC_2$; and/or the locations of model pupil centers $P_{c1}$, $P_{c2}$. FIG. 13 depicts a method 500 for fixation detection and filter updating according to a particular embodiment of the invention. Method 500 may be applied to any one or more of the filtered parameter(s) of method 100, including any of the example parameters listed above. For the purposes of explanation, it is assumed that the method 500 parameter is the three-dimensional POG determined in block 140 (FIG. 1).

Method 500 commences in block 501 where a first raw parameter (e.g. POG) value is obtained. Since there is no historical POG data, the raw POG value obtained in block 501 is used as the filtered POG value for the purposes of the final POG estimate. Method 500 then proceeds to block 502 which involves getting a new raw parameter (e.g. POG) value. In block 502, there is/are historical parameter (e.g. POG) value(s). Consequently, the raw POG value is retained, but the system applies the moving average filter to the raw POG value and uses the filtered POG value as its estimate of the user's current POG. Method 500 then proceeds to block 504. Block 504 involves an inquiry into whether there are a sufficient number (n) of raw parameter (e.g. POG) values within a first threshold region (i.e. sufficiently close to one another) to conclude that the user eyes are fixated on something. The first threshold region may be different depending on the nature of the parameter being filtered. For example, where the parameter being filtered in the POG estimate or a direction of a calibrated or uncalibrated LOS vector in the principal coordinate system, then the first threshold region may represent a region of space in the principal coordinate system. As another example, where the parameter being filtered is the center of the pupil in the fine pupil image data, then the first threshold region may represent a region of pixels in the image data.

The number n of raw POG values may vary depending on the application to which system 210 is being put to use and on the sampling rate (e.g. the rate of iteration of method 100). For example, when system 210 is being used as a pointing device for a man/machine user interface, the ratio of the number n to the sampling rate may be relatively low (e.g. in a range of 0.01-0.10 seconds), such that method 500 quickly determines new fixation locations, thereby allowing the user to interact relatively quickly with the user interface. By way of contrasting example, when system 210 is being used to evaluate the functionality of the user's eyes, the ratio of the number n to the sampling rate may be set relatively high (e.g. in a range of 0.25-4 seconds), such that a fixation is only determined by method 500 after the user has been staring at the same location for a period of time.

The dimensions of the first threshold region may also depend on the application to which system 210 is being put to use. For example, where the parameter being filtered in method 500 is the POG estimate and system 210 is being used to select between closely spaced POGs, then the dimension(s) of the first threshold region may be relatively small (e.g. less than 2 cm$^3$), such that system 210 is able to discern between different POGs without mistakenly concluding that the user is fixated on a particular POG. On the other hand, when the POG locations for which system 210 is required to discern are relatively spaced apart, then the first threshold region may be relatively large (e.g. greater than 2 cm$^3$), such that a fixation may be established relatively quickly by method 500. The center of the first threshold region may be the average of the n raw parameter (e.g. POG) values or, in some embodiments, the average of some other number of recently obtained raw parameter (e.g. POG) values.

If the block 504 inquiry determines that there is no fixation (block 504 NO ouput), then method 500 returns to block 502 to obtain another raw parameter value. If it is concluded in block 504 that a user's eyes are fixated (i.e. there are n raw parameter values within the first threshold region—block 504 YES output), then method 500 proceeds to block 506, where a fixation is established. Block 506 may involve toggling a boolean variable, for example. After block 506, method 500 proceeds to block 508 which involves obtaining another raw parameter value. Method then proceeds to block 510. Block 510 involves an inquiry into whether the block 508 raw parameter value is within a second threshold region.

If the block 510 inquiry determines that the block 508 raw parameter value is within the second threshold region (block 510 YES output), then method 500 concludes that the user is still focusing on the same region of space (i.e. the user's eyes are fixated) and the filter history is maintained, but if the block 510 inquiry determines that the block 508 raw parameter value is outside of the second threshold region (block 510 NO output), then method 500 concludes that the user is changing his or her fixation and the filter history is cleared. In general, the second threshold region used in the block 510 inquiry may be different than the first threshold region used in the block 504 inquiry, although this is not necessary. The center of the second threshold region may be the average of some suitable number of recently obtained raw parameter values. The boundary of the second threshold region may be selected on the basis of criteria similar to the above-discussed criteria used to select the boundary of the first threshold region.

If the block 508 raw parameter value is within the second threshold region (block 510 YES output), then method 500 proceeds to block 512 which involves filtering the block 508 raw parameter value and using the filtered parameter value in the estimate of the user's current POG. If, on the other hand, the block 508 raw parameter value is outside of the second threshold region (block 510 NO output), then method 500 proceeds to block 514. Block 514 involves clearing the filter history to avoid obtaining spurious results when method 500 concludes that the user is shifting their POG. After block 514, method 500 loops back to block 501 and method 500 is repeated again.

As discussed above, method 500 may be applied to a variety of parameters (e.g. other than POG) for which filtering may be desirable. In cases where method 500 is applied to other parameter(s), it may be desirable to select the characteristics on the first and second threshold regions on the basis of other criteria.

Certain implementations of the invention comprise computer processors which execute software instructions which cause the processors to perform a method of the invention. For example, one or more processors in a point of gaze estimation system may implement data processing steps in the methods described herein by executing software instructions retrieved from a program memory accessible to the processors. The invention may also be provided in the form of a program product. The program product may comprise any medium which carries a set of computer-readable instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like. The instructions may be present on the program product in encrypted and/or compressed formats.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e. that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

Blocks 142, 144 described above represent one technique for using the first and second LOS vectors ($\overline{LOS_1}$, $\overline{LOS_2}$) to determine the three-dimensional POG in block 140. In other embodiments, block 140 may be implemented using other techniques. For example, referring to FIG. 2, one can use the cross-product operator× to define a normal vector $\bar{n} = \overline{LOS_1} \times \overline{LOS_2}$ which is perpendicular to both the first and second LOS vectors ($\overline{LOS_1}$, $\overline{LOS_2}$). The magnitude of the closest distance d between the first and second LOS vectors ($\overline{LOS_1}$, $\overline{LOS_2}$) can then be determined by projecting the vector $\bar{r} = [CC_1 - CC_2]$ onto the unit normal vector $$\hat{n} = \frac{\bar{n}}{\|\bar{n}\|}$$

in accordance with $d = |\bar{r} \cdot \hat{n}|$. Referring to the vector $\overline{W} = [P(s) - Q(t)]$ shown in FIG. 2, we can then express a system of three equations:

$$\overline{LOS_1} \cdot \overline{W} = 0$$

$$\overline{LOS_2} \cdot \overline{W} = 0$$

$$\overline{W} \cdot \overline{W} = d^2$$

which may be solved for the three variables $w_x, w_y, w_z$ where $\overline{W} = [w_x, w_y, w_z]$. It should be noted that because of the $d^2$ term, there will be two solutions to the above system of equations. Recognizing, from the above discussion, that $P(s) = [\overline{CC_1} + s\overline{LOS_1}]$ and $Q(t) = [\overline{CC_2} + t\overline{LOS_2}]$, one may divide the equation $\overline{W} = [P(s) - Q(t)]$ into its component parts (i.e. $w_x = CC_{1,x} + sLOS_{1,x} - CC_{2,x} - tLOS_{2,x}$, $w_y = CC_{1,y} + sLOS_{1,y} - CC_{2,y} - tLOS_{2,y}$, $w_z = CC_{1,z} + sLOS_{1,z} - CC_{2,z} - tLOS_{2,z}$) to yield three equations in two unknowns (s, t). This system may be solved to yield s and t, which in turn may be used to calculate P(s), Q(t) and $\overline{W}$. The three-dimensional POG can then be determined to be the midpoint of $\overline{W}$ (between the points P(s) and Q(t)).

The FIR moving average filters described above may be replaced with other suitable types of filters which may serve to reduce high frequency jitter in the method 100 POG estimation.

Some of the methods described above (e.g. method 400 (FIG. 4), method 350 (FIG. 6), method 370 (FIG. 6), method 400 (FIG. 8), method 600 (FIGS. 17A, 17B), method 440 (FIG. 9) and method 480 (FIG. 12)) are shown and described in relation to one of the user's eyes, but it will be appreciated that these methods may be applied in a similar manner to the other one of the user's eyes. Others of the methods described above (e.g. method 100 (FIG. 1), method 460 (FIG. 11) and method 500 (FIG. 13)) may involve both of the user's eyes.

In some applications, various aspects of the geometry of objects within the scene presented to the user may be known. By way of non-limiting example, where the scene presented to the user includes a computer screen, the screen may be described in three dimensions by a planar surface in the principal coordinate system provided that three points on the screen are known and that the boundary of the screen is known. As another non-limiting example, a round ball may be represented by a spherical surface with a known center and a known radius in the principal coordinate system. Objects of general shape may be described using a fine mesh of polygons, whose polygonal characteristics are known in the principal coordinate system. In cases where the geometry of the scene or objects in the scene is known, then it is possible to estimate a three-dimensional POG by determining the intersection of a single LOS vector ($\overline{LOS_1}$, $\overline{LOS_2}$) with the known geometry of an object in the scene. Once an LOS vector ($\overline{LOS_1}$, $\overline{LOS_2}$) is determined in the principal coordinate system, then geometrical calculations may be performed to determine the intersection point(s) of one of the LOS vectors with objects of known geometry. Such geometrical calculations are well known in the art and depend on the geometry of the object in the scene. In some applications, accuracy and/or precision may be improved by determining LOS vectors ($\overline{LOS_1}$, $\overline{LOS_2}$) for both eyes, determining the intersection point(s) of both LOS vectors ($\overline{LOS_1}$, $\overline{LOS_2}$) with the known geometry of the object in the scene and averaging corresponding intersection points from both eyes to arrive at the three-dimensional POG estimate. As discussed above, the same scene is preferably presented to both of the user's eyes. The scene presented to the user may be the real world.

Certain features of the systems and methods described herein are applicable to detecting a single LOS vector and using the single LOS vector in combination with known objects in the scene (e.g. a planar monitor screen or another object with a known geometry) to predict the user's POG in the scene. For example, a POG may be determined to be the point where a single LOS vector intersects the known location of the object. Particular features which may be used in connection with a single LOS include, without limitation: methods for obtaining fine pupil particulars in the image data (FIGS. 4, 6, 7 and 8), methods for obtaining glint particulars in the image data (FIGS. 4 and 7), calibration methods (FIGS. 9, 10, 11, 12, 14 and 15), filtering methods (FIG. 13) and methods for mapping glints detected in the image data to particular off-axis lights (FIGS. 16, 17 and 18).

Accordingly, the invention should be construed in accordance with the following claims.

What is claimed is:

1. A method for determining a point-of-gaze (POG) of a user in three dimensions, the method comprising:
   presenting a three-dimensional scene to the user;
   capturing image data which includes images of both eyes of the user using a single image capturing device;
   estimating a first line-of-sight (LOS) vector in a three-dimensional coordinate system for a first of the user's eyes based on the image data captured by the single image capturing device;
   estimating a second LOS vector in the three-dimensional coordinate system for a second of the user's eyes based on the image data captured by the single image capturing device;
   determining the three-dimensional POG of the user in the scene in the three-dimensional coordinate system using the first and second LOS vectors as estimated based on the image data captured by the single image capturing device;
   wherein determining the three-dimensional POG in the three-dimensional coordinate system comprises:
   determining a third vector in the three-dimensional coordinate system which intersects the first and second LOS vectors and is orthogonal to both the first and second LOS vectors;
   estimating the three-dimensional POG to be the midpoint of the third vector.

2. A method according to claim 1 wherein the scene is a region of the real world and the three-dimensional coordinate system is a system for identifying a location of one or more points in the real world.

3. A method according to claim 1 wherein the scene comprises a region of the real world in which a virtual scene is displayed and the three-dimensional coordinate system is a system for identifying a location of one or more points in the virtual scene based on a corresponding location of the one or more points in the real world.

4. A method according to claim 1 wherein estimating the first and second LOS vectors comprises, for each eye, using a plurality of image features within the image data to estimate a center of the cornea of the eye in the three-dimensional coordinate system.

5. A method according to claim 4 wherein, for each eye, the plurality of image features comprises a corresponding plurality of glints and each glint comprises a reflection of a corresponding light source from the eye.

6. A method according to claim 5 wherein each light source is positioned at a corresponding off-axis location that is spaced apart from an optical axis of an image capturing device which captures the image data.

7. A method according to claim 1 wherein estimating the first and second LOS vectors comprises, for each eye:
detecting a plurality of glints within the image data, each glint comprising a reflection from the eye;
establishing a correspondence between each of the glints and a corresponding light source;
using at least two of the plurality of glints and the correspondence between the at least two glints and their corresponding light sources to estimate a center of the cornea of the eye in the three-dimensional coordinate system.

8. A method according to claim 7 wherein each light source is positioned at a corresponding off-axis location that is spaced apart from an optical axis of an image capturing device which captures the image data.

9. A method according to claim 8 wherein the off-axis locations of the light sources are non-symmetrically distributed about the optical axis.

10. A method according to claim 7 wherein, for each eye, establishing the correspondence between each of the glints and the corresponding light source comprises performing a pattern matching process between the detected plurality of glints and a plurality of reference points wherein a correspondence between the reference points and the light sources is known.

11. A method for determining a point-of-gaze (POG) of a user in three dimensions, the method comprising:
presenting a three-dimensional scene to the user;
capturing image data which includes images of both eyes of the user using a single image capturing device;
estimating a first line-of-sight (LOS) vector in a three-dimensional coordinate system for a first of the user's eyes based on the image data captured by the single image capturing device;
estimating a second LOS vector in the three-dimensional coordinate system for a second of the user's eyes based on the image data captured by the single image capturing device;
determining the three-dimensional POG of the user in the scene in the three-dimensional coordinate system using the first and second LOS vectors as estimated based on the image data captured by the single image capturing device;
wherein estimating the first and second LOS vectors comprises, for each eye:
detecting a plurality of glints within the image data, each glint comprising a reflection from the eye;
establishing a correspondence between each of the glints and a corresponding light source;
using at least two of the plurality of glints and the correspondence between the at least two glints and their corresponding light sources to estimate a center of the cornea of the eye in the three-dimensional coordinate system;
wherein, for each eye, establishing the correspondence between each of the glints and the corresponding light source comprises performing a pattern matching process between the detected plurality of glints and a plurality of reference points wherein a correspondence between the reference points and the light sources is known; and
wherein, for each eye, performing the pattern matching process comprises:
(a) analyzing the image data to estimate a center of a pupil image of the eye within the image data;
(b) determining a translation between a glint closest to the center of the pupil image and a particular one of the reference points;
(c) temporarily applying the translation to the glints other than the glint closest to the center of the pupil image to obtain a set of translated glints;
(d) evaluating distances between the translated glints and the reference points other than the particular one of the reference points;
(e) if any particular distance is less than a pattern matching threshold, then assigning a correspondence between the translated glint and the reference point separated by the particular distance; and
(f) repeating steps (b) through (e) with the particular one of the reference points replaced by a different one of the reference points until each of the reference points has been the particular one of the reference points.

12. A method according to claim 11 wherein if evaluating distances between the translated glints and the reference points other than the particular one of the reference points determines that one of the distances is a global minimum distance, then assigning a correspondence between the glint closest to the center of the pupil image and the particular one of the reference points.

13. A method according to claim 7 wherein using the glints and the correspondence between the glints and their corresponding light sources to estimate a center of the cornea of the eye in the three-dimensional coordinate system comprises selecting a subset plurality of glints from among the plurality of glints and using the subset plurality of glints and the correspondence between the subset plurality of glints and its corresponding light sources to estimate the center of the cornea of the eye in the three-dimensional coordinate system and wherein selecting the subset plurality of glints from among the plurality of glints comprises: analyzing the image data to estimate a center of a pupil image of the eye within the image data and choosing the subset plurality of glints closest to the center of the pupil image.

14. A method according to claim 13 wherein the subset plurality of glints comprises two glints.

15. A method according to claim 13 wherein, for each eye, establishing the correspondence between each of the glints and the corresponding light source comprises performing a pattern matching process between the detected plurality of glints and a plurality of reference points wherein a correspondence between the reference points and the light sources is known.

16. A method for determining a point-of-gaze (POG) of a user in three dimensions, the method comprising:
presenting a three-dimensional scene to the user;
capturing image data which includes images of both eyes of the user using a single image capturing device;
estimating a first line-of-sight (LOS) vector in a three-dimensional coordinate system for a first of the user's eyes based on the image data captured by the single image capturing device;
estimating a second LOS vector in the three-dimensional coordinate system for a second of the user's eyes based on the image data captured by the single image capturing device;
determining the three-dimensional POG of the user in the scene in the three-dimensional coordinate system using the first and second LOS vectors as estimated based on the image data captured by the single image capturing device;
wherein estimating the first and second LOS vectors comprises, for each eye:
detecting a plurality of glints within the image data, each glint comprising a reflection from the eye;
establishing a correspondence between each of the glints and a corresponding light source;
using at least two of the plurality of glints and the correspondence between the at least two glints and their corresponding light sources to estimate a center of the cornea of the eye in the three-dimensional coordinate system;
wherein using the glints and the correspondence between the glints and their corresponding light sources to estimate a center of the cornea of the eye in the three-dimensional coordinate system comprises selecting a subset plurality of glints from among the plurality of glints and using the subset plurality of glints and the correspondence between the subset plurality of glints and its corresponding light sources to estimate the center of the cornea of the eye in the three-dimensional coordinate system and wherein selecting the subset plurality of glints from among the plurality of glints comprises:
analyzing the image data to estimate a center of a pupil image of the eye within the image data and choosing the subset plurality of glints closest to the center of the pupil image;
wherein, for each eye, establishing the correspondence between each of the glints and the corresponding light source comprises performing a pattern matching process between the detected plurality of glints and a plurality of reference points wherein a correspondence between the reference points and the light sources is known; and
wherein, for each eye, performing the pattern matching process comprises:
(a) determining a translation between a glint closest to the center of the pupil image and a particular one of the reference points;
(b) temporarily applying the translation to the glints other than the glint closest to the center of the pupil image to obtain a set of translated glints;
(c) evaluating distances between the translated glints and the reference points other than the particular one of the reference points;
(d) if any particular distance is less than a pattern matching threshold, then assigning a correspondence between the translated glint and the reference point separated by the particular distance; and
(e) repeating steps (a) through (d) with the particular one of the reference points replaced by a different one of the reference points until each of the reference points has been the particular one of the reference points.

17. A method according to claim 16 wherein if evaluating distances between the translated glints and the reference points other than the particular one of the reference points determines that one of the distances is a global minimum distance, then assigning a correspondence between the glint closest to the center of the pupil image and the particular one of the reference points.

18. A method according to claim 4 comprising, for each eye, analyzing the image data to estimate characteristics of a pupil image of the eye within the image data.

19. A method according to claim 18 wherein, for each eye, analyzing the image data to estimate characteristics of the pupil image within the image data comprises estimating a center of the pupil image in the image data and wherein estimating the first and second LOS vectors comprises, for each eye, tracing a ray from the center of the pupil image in the image data into a model of the eye in the three-dimensional coordinate system to estimate a location of a center of the pupil in the three-dimensional coordinate system.

20. A method for determining a point-of-gaze (POG) of a user in three dimensions, the method comprising:
presenting a three-dimensional scene to the user;
capturing image data which includes images of both eyes of the user using a single image capturing device;
estimating a first line-of-sight (LOS) vector in a three-dimensional coordinate system for a first of the user's eyes based on the image data captured by the single image capturing device;
estimating a second LOS vector in the three-dimensional coordinate system for a second of the user's eyes based on the image data captured by the single image capturing device;
determining the three-dimensional POG of the user in the scene in the three-dimensional coordinate system using the first and second LOS vectors as estimated based on the image data captured by the single image capturing device;
wherein estimating the first and second LOS vectors comprises, for each eye, using a plurality of image features within the image data to estimate a center of the cornea of the eye in the three-dimensional coordinate system;
the method further comprising, for each eye, analyzing the image data to estimate characteristics of a pupil image of the eye within the image data;
wherein, for each eye, analyzing the image data to estimate characteristics of the pupil image within the image data comprises estimating a perimeter of the pupil image in the image data and wherein estimating the first and second LOS vectors comprises, for each eye:
tracing a plurality of rays from the perimeter of the pupil image in the image data to corresponding locations in a model of the eye in the three-dimensional coordinate system; and
taking an average of the corresponding locations to determine a center of the pupil in the three-dimensional coordinate system.

21. A method according to claim 19 wherein estimating the first and second LOS vectors comprises, for each eye, determining the LOS vector to be on a line from the center of the cornea of the eye through the center of the pupil of the eye in the three-dimensional coordinate system.

22. A method for determining a point-of-gaze (POG) of a user in three dimensions, the method comprising:
presenting a three-dimensional scene to the user;
capturing image data which includes images of both eyes of the user using a single image capturing device;
estimating a first line-of-sight (LOS) vector in a three-dimensional coordinate system for a first of the user's eyes based on the image data captured by the single image capturing device;
estimating a second LOS vector in the three-dimensional coordinate system for a second of the user's eyes based on the image data captured by the single image capturing device;
determining the three-dimensional POG of the user in the scene in the three-dimensional coordinate system using the first and second LOS vectors as estimated based on the image data captured by the single image capturing device;
wherein estimating the first and second LOS vectors comprises, for each eye, using a plurality of image features within the image data to estimate a center of the cornea of the eye in the three-dimensional coordinate system; and
wherein, for each eye, using the glints and the correspondence between the glints and their corresponding light sources to estimate a center of the cornea of the eye in the three-dimensional coordinate system comprises using a model of the eye where one or more parameters of the model of the eye are based on population averages.

23. A method according to claim 4 wherein, for each eye, using the glints and the correspondence between the glints and their corresponding light sources to estimate a center of the cornea of the eye in the three-dimensional coordinate system comprises using a model of the eye where one or more parameters of the model of the eye are measured from the user's eye.

24. A method according to claim 1 wherein capturing the image data comprises:
capturing a dark pupil image illuminated by a plurality of off-axis light sources, the off-axis light sources being positioned at locations away from an optical axis of an image-capturing device that captures the image data; and
capturing a bright pupil image illuminated by one or more on-axis light sources, the one or more on-axis light sources being positioned at one or more corresponding locations relatively close to the optical axis when compared to the locations of the off-axis light sources.

25. A method for determining a point-of-gaze (POG) of a user in three dimensions, the method comprising:
presenting a three-dimensional scene to the user;
capturing image data which includes images of both eyes of the user using a single image capturing device;
estimating a first line-of-sight (LOS) vector in a three-dimensional coordinate system for a first of the user's eyes based on the image data captured by the single image capturing device;
estimating a second LOS vector in the three-dimensional coordinate system for a second of the user's eyes based on the image data captured by the single image capturing device;
determining the three-dimensional POG of the user in the scene in the three-dimensional coordinate system using the first and second LOS vectors as estimated based on the image data captured by the single image capturing device;
wherein capturing the image data comprises:
capturing a dark pupil image illuminated by a plurality of off-axis light sources, the off-axis light sources being positioned at locations away from an optical axis of an image-capturing device that captures the image data; and
capturing a bright pupil image illuminated by one or more on-axis light sources, the one or more on-axis light sources being positioned at one or more corresponding locations relatively close to the optical axis when compared to the locations of the off-axis light sources; and
wherein estimating the first and second LOS vectors comprises, for each eye:
subtracting intensity values of pixels in the dark pupil image from intensity values of pixels in the bright pupil image to obtain a difference image; and
applying a binary thresholding process to the difference image to obtain rough pupil binarized data, wherein pixels of the difference image having intensity values greater than a difference image threshold are assigned a first binary value in the rough pupil binarized data and pixels of the difference image having intensity values less than the difference image threshold are assigned a second binary value in the rough pupil binarized data.

26. A method according to claim 25 comprising, for each eye, locating a glint corresponding to at least one of the one or more on-axis light sources in the bright pupil image, wherein locating the glint comprises:
locating a maximum intensity pixel in the bright pupil image;
determining a bright pupil threshold glint intensity level, the bright pupil threshold glint intensity level based at least in part on an average of intensities of pixels in a region surrounding the maximum intensity pixel; and
using the bright pupil threshold glint intensity level to obtain a bright pupil binarized glint profile wherein pixels having intensities greater than the bright pupil threshold glint intensity level are assigned a first binary value and pixels having intensities less than the bright pupil threshold glint intensity level are assigned a second binary value.

27. A method according to claim 26 comprising, for each eye, locating two or more dark pupil glints corresponding to two or more of the plurality of off-axis light sources in the dark pupil image.

28. A method according to claim 27 comprising, for each eye, determining a fine pupil threshold, wherein determining the fine pupil threshold comprises:
performing a logical AND operation of the rough pupil binarized data and an inverse of the bright pupil binarized glint profile to obtain a pupil mask;
applying the pupil mask to the bright pupil image to obtain masked bright pupil data, wherein the masked bright pupil data permits identification of pixels in the bright pupil image which correspond to the pupil of the eye and which are not part of the glint; and
using the masked bright pupil data to calculate the fine pupil threshold, the fine pupil threshold calculated at least in part by averaging intensities of the pixels in the bright pupil image which correspond to the pupil of the eye and which are not part of the glint.

29. A method according to claim 28 comprising, for each eye, determining fine pupil binarized data, wherein determining fine pupil binarized data comprises:

applying the fine pupil threshold to the bright pupil image to obtain a binarized fine pupil profile wherein pixels of the bright pupil image having intensities greater than the fine pupil threshold are assigned a first binary value and pixels of the bright pupil image having intensities less than the fine pupil threshold are assigned a second binary value; and performing a logical AND operation of the binarized fine pupil profile and an inverse of the bright pupil binarized glint profile to obtain the fine pupil binarized data.

30. A method according to claim 29 comprising, for each eye, locating a contour in the fine pupil binarized data corresponding to the pupil; and fitting an ellipse to the contour to obtain a fine description of the perimeter of the pupil.

31. A method according to claim 30 wherein estimating the first and second LOS vectors comprises, for each eye, using the locations of at least two of the two or more dark pupil glints in the dark pupil image to estimate a center of the cornea of the eye in the three-dimensional coordinate system.

32. A method according to claim 31 wherein estimating the first and second LOS vectors comprises, for each eye:
using the fine description of the perimeter of the pupil of the eye to estimate a center of the pupil in the image data;
tracing a ray from the center of the pupil in the image data into a model of the eye in the three-dimensional coordinate system to estimate a location of a center of the pupil of the eye in the three-dimensional coordinate system.

33. A method according to claim 31 wherein estimating the first and second LOS vectors comprises, for each eye:
tracing a plurality of rays from the fine description of the perimeter of the pupil of the eye in the image data to corresponding locations in a model of the eye in the three-dimensional coordinate system; and
taking an average of the corresponding locations to determine a center of the pupil of the eye in the three-dimensional coordinate system.

34. A method according to claim 32 wherein estimating the first and second LOS vectors comprises, for each eye: determining the LOS vector to be on a line from the center of the cornea of the eye through the center of the pupil of the eye in the three-dimensional coordinate system.

35. A method according to claim 1 comprising, for each eye, adjusting the LOS vector in the three-dimensional coordinate system using one or more weighted calibration values to obtain a calibrated LOS vector.

36. A method for determining a point-of-gaze (POG) of a user in three dimensions, the method comprising:
presenting a three-dimensional scene to the user;
capturing image data which includes images of both eyes of the user using a single image capturing device;
estimating a first line-of-sight (LOS) vector in a three-dimensional coordinate system for a first of the user's eyes based on the image data captured by the single image capturing device;
estimating a second LOS vector in the three-dimensional coordinate system for a second of the user's eyes based on the image data captured by the single image capturing device;
determining the three-dimensional POG of the user in the scene in the three-dimensional coordinate system using the first and second LOS vectors as estimated based on the image data captured by the single image capturing device; and
for each eye, adjusting the LOS vector in the three-dimensional coordinate system using one or more weighted calibration values to obtain a calibrated LOS vector; and for each eye:
determining one or more calibration values, each calibration value determined at least in part by performing a difference calculation between a corresponding estimated calibration LOS vector in the three-dimensional coordinate system when the user is fixated on a corresponding reference point in the scene and a LOS vector that would intersect the corresponding reference point in the three-dimensional coordinate system;
determining a weight for each of the one or more calibration values, each weight based at least in part on a distance between the LOS vector and the corresponding estimated calibration LOS vector in the three-dimensional coordinate system; and
multiplying each calibration value by its corresponding weight to determine the one or more weighted calibration values.

37. A method according to claim 35 wherein determining the three-dimensional POG of the user in the scene in the three-dimensional coordinate system comprises, for each of the first and second LOS vectors, using the calibrated LOS vector in place of the LOS vector.

38. A method according to claim 1 comprising applying a moving average filter to successive estimations of at least one of: the POG in the three-dimensional coordinate system; the first LOS vector in the three-dimensional coordinate system; and the second LOS vector in the three-dimensional coordinate system; to obtain a filtered three-dimensional POG.

39. A method according to claim 38 comprising clearing historical values from the moving average filter upon determining that the user has changed from a first fixation location to a second fixation location.

40. A method for determining a point-of-gaze (POG) of a user in three dimensions, the method comprising:
presenting a three-dimensional scene to the user;
capturing image data which includes images of both eyes of the user using a single image capturing device;
estimating a first line-of-sight (LOS) vector in a three-dimensional coordinate system for a first of the user's eyes based on the image data captured by the single image capturing device;
estimating a second LOS vector in the three-dimensional coordinate system for a second of the user's eyes based on the image data captured by the single image capturing device;
determining the three-dimensional POG of the user in the scene in the three-dimensional coordinate system using the first and second LOS vectors as estimated based on the image data captured by the single image capturing device;
applying a moving average filter to successive estimations of at least one of: the POG in the three-dimensional coordinate system; the first LOS vector in the three-dimensional coordinate system; and the second LOS vector in the three-dimensional coordinate system; to obtain a filtered three-dimensional POG; and
clearing historical values from the moving average filter upon determining that the user has changed from a first fixation location to a second fixation location;
wherein determining that the user has changed from the first fixation location to the second fixation location comprises at least one of:
comparing each successive estimate of the POG in the three-dimensional coordinate system to a threshold POG region and concluding that the user has changed fixations when the estimated POG in the three-dimensional coordinate system is outside the threshold POG region;

comparing each successive first LOS in the three-dimensional coordinate system to a threshold first LOS region and concluding that the user has changed fixations when the first LOS in the three-dimensional coordinate system is outside the threshold first LOS region; and comparing each successive second LOS in the three-dimensional coordinate system to a threshold second LOS region and concluding that the user has changed fixations when the second LOS in the three-dimensional coordinate system is outside the threshold second LOS region.

41. A method according to claim 20 wherein estimating the first and second LOS vectors comprises, for each eye, determining the LOS vector to be on a line from the center of the cornea of the eye through the center of the pupil of the eye in the three-dimensional coordinate system.

42. A method according to claim 33 wherein estimating the first and second LOS vectors comprises, for each eye: determining the LOS vector to be on a line from the center of the cornea of the eye through the center of the pupil of the eye in the three-dimensional coordinate system.

* * * * *